US008372597B2

(12) United States Patent
Francis et al.

(10) Patent No.: US 8,372,597 B2
(45) Date of Patent: *Feb. 12, 2013

(54) METHODS OF SCREENING FOR INTRODUCTION OF DNA INTO A TARGET CELL

(75) Inventors: Kevin P. Francis, Alameda, CA (US); Timothy C. Doyle, Alameda, CA (US); Kevin A. Nawotka, Alameda, CA (US)

(73) Assignee: Xenogen Corporation, Alameda, CA (US)

(*) Notice: Subject to any disclaimer, the term of this patent is extended or adjusted under 35 U.S.C. 154(b) by 246 days.

This patent is subject to a terminal disclaimer.

(21) Appl. No.: 11/429,391

(22) Filed: May 4, 2006

(65) Prior Publication Data
US 2007/0010018 A1    Jan. 11, 2007

Related U.S. Application Data

(63) Continuation of application No. 10/094,146, filed on Mar. 7, 2002, now Pat. No. 7,090,994.

(60) Provisional application No. 60/274,094, filed on Mar. 7, 2001, provisional application No. 60/292,828, filed on May 22, 2001.

(51) Int. Cl.
*C12Q 1/66* (2006.01)
*C12N 15/00* (2006.01)
*C12N 15/81* (2006.01)

(52) U.S. Cl. .... 435/8; 435/254.22; 435/69.1; 435/320.1

(58) Field of Classification Search .......................... None
See application file for complete search history.

(56) References Cited

U.S. PATENT DOCUMENTS

| | | | |
|---|---|---|---|
| 5,639,603 A | 6/1997 | Dower et al. | |
| 5,968,750 A | 10/1999 | Zolotukhin et al. | |
| 5,994,077 A | 11/1999 | Valdivia et al. | |
| 6,096,505 A | 8/2000 | Selby et al. | |
| 6,232,107 B1 * | 5/2001 | Bryan et al. | 435/189 |
| 6,303,344 B1 * | 10/2001 | Patten et al. | 435/91.1 |
| 6,605,430 B1 | 8/2003 | Affholter et al. | |
| 6,737,245 B1 | 5/2004 | Francis et al. | |
| 7,056,728 B2 * | 6/2006 | Francis et al. | 435/320.1 |
| 7,090,994 B2 * | 8/2006 | Francis et al. | 435/8 |
| 2001/0008759 A1 | 7/2001 | Marks et al. | |
| 2002/0090605 A1 | 7/2002 | Kamb | |
| 2002/0137215 A1 | 9/2002 | Francis et al. | |
| 2002/0138855 A1 | 9/2002 | Zhang et al. | |
| 2002/0192635 A1 | 12/2002 | Aubrecht et al. | |
| 2003/0003143 A1 | 1/2003 | Papahadjopoulos et al. | |
| 2003/0039990 A1 | 2/2003 | Schuur | |
| 2004/0005564 A1 | 1/2004 | Mauro et al. | |
| 2005/0066377 A1 * | 3/2005 | Zambrowicz et al. | 800/8 |

FOREIGN PATENT DOCUMENTS

| | | |
|---|---|---|
| WO | WO 97/18841 | 5/1997 |
| WO | WO 01/71040 | 9/2001 |

OTHER PUBLICATIONS

Bell et al., "Facilitating Functional Analysis of the *Saccharomyces cerevisiae* Genome Using and EGFP-Based Promoter Library and Flow Cytometry," *Yeast*, 15:1747-1759 (1999).
Care et al., "The Met3 Promoter: Anew Tool for *Candida albicans* Molecular Genetics," *Molecular Microbiology*. 34(4):792-798 (1999).
Cormack, B. et al., "Yeast-Enhanced Green Fluorescent Protein (yEGFP): A Reporter of Gene Expression in *Candida albicans*," *Microbiology*, 143: 303-311, 1997.
Hautefort and Hinton, "Measurement of Bacterial Gene Expression in vivo," *Philos Trans R Soc Lond B Biol Sci*, 355(1397): 601-611 (2000).
Ignacimuthu et al., "Detection of Firefly Liciferase Activit in Rice Callus Using CCD Camera," *Indian Journal of Experimental Biology*, 36:920-023 (1998).
Morschhauser, J. et al., "Expression of a Chromosomally Integrated, Single-Copy GFP Gene in *Candida albicans*, and Its Use As a Reporter of Gene Regulation," *Mol Gen Gene*, 257: 412-420,1998.
Srikantha, T. et al., "The Sea Pansy *Renilla reniformis* Luciferase Serves as a Sensitive Bioluminescent Reporter for Differential Gene Expression in *Candida albicans*," *Journal of Bacteriology*, 178: 121-129, 1996.
Svensonn and Akusjarvi, "Adenovirus VA RNAI Mediates a Translational Stimulation Which Is Not Restricted to the Viral mRNAs," *EMBO Journal*, Vcol4(4): 957-964 (1985).
Tenhami, et al., "Measurement of Effects of Antibiotics in Bioluminescent *Staphylococcus aureus* RN4220," *Antimicrobial Agents and Chemotherapy*, 45(12):3456-3461 (2001).
Welsh and Kay, "Reporter Gene Expression for Monitoring Gene Transfer," *Current Opinion in Biotech*, 8:617-622 (1997).
Wirtz, et al., "A Tightly Regulated Inducible Expression System for Conditional Gene Knock-Outs and Dominant Negatove Genetics in *Trypansoma brucei*," *Molecular and Biochemical Parsitology*, 99:89-101 (1999).

* cited by examiner

*Primary Examiner* — Maria Marvich
(74) *Attorney, Agent, or Firm* — Pasternak Patent Law; Dahna S. Pasternak

(57) ABSTRACT

The present invention provides methods of introducing a polynucleotide into a target cell, wherein the method employs a light generating protein coding sequence acting as a reporter. An important advantage of the methods described herein is that drug resistant target cells or target cells having no useful auxotrophic markers can be effectively transformed. The present invention also includes transformed cells produced by the methods described herein. Also described are light generating protein coding sequence modifications, a variety of vectors, and methods of using the transformed cells of the present invention.

4 Claims, 6 Drawing Sheets

Figure 1

| | |
|---|---|
| XR1T | CCGCTGGAGAGCAATTGCATAAGGCT (SEQ ID NO:5) |
| XR1B | AGCCTTATGCAATTGCTCTCCAGCGG (SEQ ID NO:6) |
| XR2T | GAAGAGATACGCCTTGGTTCCTGG (SEQ ID NO:7) |
| XR2B | CCAGGAACCAAGGCGTATCTCTTC (SEQ ID NO:8) |
| XR3T | AAACGATATGGGTTGAATACAAATCAC (SEQ ID NO:9) |
| XR3B | GTGATTTGTATTCAACCCATATCGTTT (SEQ ID NO:10) |
| XR4T | GTGACAAAACAATTGCATTGATAATGA (SEQ ID NO:11) |
| XR4B | TCATTATCAATGCAATTGTTTTGTCAC (SEQ ID NO:12) |
| RR1T | GATTTGAAGAAGAGTTGTTTTACGATCCCTT (SEQ ID NO:13) |
| RR1B | AAGGGATCGTAAAAACAACTCTTCTTCAAATC (SEQ ID NO:14) |
| RR2T | CGCCAAAAGCAC<u>A</u>TTGATTGACAAATA (SEQ ID NO:15) |
| RR2B | TATTTGTCAATCAA<u>T</u>GTGCTTTTGGCG (SEQ ID NO:16) |
| RR3T | AGACTACATC<u>T</u>GCTATTTTGATTACACCC (SEQ ID NO:17) |
| RR3B | GGGTGTATTCAAAATAGC<u>A</u>GATGTAGTCT (SEQ ID NO:18) |

RR45T
    AGGTTGTGGATTTGGATAC<u>A</u>GGGAAAAC<u>T</u>TTGGGCGTTAATCAGA
    (SEQ ID NO:19)

RR45B
    TCTGATTAACGCCCAA<u>A</u>GTTTTCCC<u>T</u>GTATCCAAATCCACAACCT
    (SEQ ID NO:20)

Figure 2A

GGCCGCATTGGCGCGCCTATAAGCTTCACATCTGGCCGGCCGACTCCTGCAGGATCTC
Not I      Asc I         Hind III         Fse I        Sbf I      Xho I
(synthetic linker A;SEQ ID NO:34)

TCGAGAGATCCTGCAGGAGTGGGCCGGCCAGATGAAGCTTATAGGCGCGCCAATGCGGCC
Xho I        Sbf I           Fse I         Hind III       Asc I I      Not I
(synthetic linker B;SEQ ID NO:35)

ENOA (SEQ ID NO:22)
TAGGGCGCGCCAGATTTGTTTACAGGTGATGCTT                    Asc I

ENOB (SEQ ID NO:23)
TATGGATCCTGTTGTAATATTCCTGAATTATCA                     Bam HI

LUCB (SEQ ID NO:24)
TGGGGATCCATGGAAGACGCCAAAAACATAAAGAAAGG                Bam HI

LUCP (SEQ ID NO:25)
TATGCTGCAGTTACAATTTGGACTTTCCGC                        Pst I

ACT-TP (SEQ ID NO:26)
GTTCTGCAGGAGTGAAATTCTGGAAATCT                         Pst I

ACT-TH (SEQ ID NO:27)
GTTAAGCTTTTTATGGAATGAATGGGATG                         Hind III URAH (SEQ ID NO:28)
GTAAAGCTTACTAATAGGAATTGATTTGGATGGT                    Hind III URAF (SEQ ID NO:29)
GTACGGCCGGCCAGGACCACCTTTGATTGTAAATAG                  Fse I

Figure 2B

TAR5N (SEQ ID NO:30)
GTA<u>GCGGCCGC</u>GAGGAGTAAAACTTTTCCAATTAAC          *Not* I

TAR5A (SEQ ID NO:31)
GTA<u>GGCGCGCC</u>ACTTTTTCTTCATTACCATAAACCC           *Asc* I

TAR3F (SEQ ID NO:32)
GTAT<u>GGCCGGCC</u>TTGAGATAAGTAGGGTTTGATAGCC          *Fse* I

TAR3S (SEQ ID NO:33)
ATGT<u>CCTGCAGG</u>CTCGGGTACCACACTGTTAGATAAA           Sbf I

Figure 2C

```
 Not I     Asc I         HindIII      Fse I          Sbf I          Xho I
GGCCGG A T T GGCGCGCC TA T AAGCTT CATCT GGCCGGCC CACT CCTGCAGG ATCT C
       C G TAA CCGCGCGG ATA T TCGAA GTAGA CCGGCCGG GTGA GGACGTCC TAGA GAGCT
```

METHODS OF SCREENING FOR INTRODUCTION OF DNA INTO A TARGET CELL

CROSS-REFERENCE TO RELATED APPLICATIONS

This application is a continuation application of U.S. patent application Ser. No. 10/094,146 filed Mar. 7, 2002 now U.S. Pat. No. 7,090,944, which claims benefit of U.S. Provisional Patent Application Ser. Nos. 60/274,094, filed Mar. 7, 2001 and 60/292,828, filed May 22, 2001 from both of which priority is claimed under 35 USC §119(e)(1), and which applications are incorporated herein by reference in their entireties.

TECHNICAL FIELD

The present invention generally relates to compositions and methods useful for detecting any target cell or organism that has been transformed with exogenous nucleic acids without the need for selectable markers. These compositions and methods allow for the introduction of DNA into any transformable cell type and the subsequent use of such cells for high-throughput screening of drugs or other compounds.

BACKGROUND OF THE INVENTION

Assays that rapidly and efficiently identify cells that have been successfully transformed with exogenous DNA are useful in a wide variety of applications including, for example, identifying cell lines and/or transgenic organisms and conducting high-throughput drug screening. Indeed, it is only once the insertion of the exogenous DNA is confirmed that cell lines or transgenic organisms can be used as animal models for drug discovery, elucidation of biochemical pathways, toxicity studies and the like.

The most commonly used method for detecting whether exogenous nucleic acid has been introduced into a target cell is by selection, either by a nutritional deficiency that is complemented by the introduced DNA, or by drug resistance. For complementation of auxotrophic mutants, the recipient cells have to be deficient in that gene function. For drug resistance, the cells have to be sensitive to that drug. Unfortunately, many cells (e.g., pathogens) are resistant to drug selection techniques. Candida albicans, for example, displays resistance to hygromycin, benomyl, cycloheximide, mitomycin C and tunicamycin. Similarly, other pathogenic organisms (e.g., methicillin-resistant Staphylococcus aureus (MRSA), and some variants of M. tuberculosis) have developed resistance to many of these routinely used antibiotics. Thus, it has proven very difficult to transform these cells and to detect successful integration events.

Methicillin-resistant strains of Staphylococcus aureus (MRSA) are the most common nosocomial pathogens worldwide. MRSA are responsible for greater than 40% of hospital-born staphylococcal infections in large, U.S., teaching hospitals. They have become prevalent in smaller hospitals (20% incidence in hospitals with 200 to 500 beds), as well as in nursing homes (Wenzel et al., 1992, Am. J. Med. 91(Supp 3B):221-227). An unusual property of MRSA strains is their ability to pick up additional resistance factors resulting in little or no susceptibility of these strains to chemotherapeutically useful antibiotics. Such multi-resistant strains of bacteria are now prevalent world-wide and the worst of these pathogens carry resistance mechanisms to all but one (i.e., vancomycin) of the usable antibacterial agents (Blumberg et al., 1991, J. Inf. Disease (63:1279-1285).

Another nosocomial pathogen, *Enterococcus faecium*, is known for its ability to transfer from one cell to another plasmid-born resistance factors, such as, vancomycin resistance. Such a mechanism for the transfer of resistance factors will lead to more and more bacterial resistant to known antibiotics. High-level vancomycin-resistance strains of *E. faecium* were first isolated in England in 1986. In 1990s, Vancomycin-resistant enterococci (VRE) were documented as having been spread all over the world. The identification of multidrug-resistant strains, which are resistant to high concentrations of ampicillin or gentamicin, or to vancomycin, introduces serious therapeutic dilemmas. Further, the absence of sensitivity to antibiotics greatly interferes with the ability to manipulate these organisms, particularly in view of the fact that most bacterial transformation vectors rely on antibiotic resistant selection. A more complete explanation of the basis for antibiotic resistance and the emergence of resistant strains can be found in the literature (e.g., U.S. Pat. No. 6,136,587 Tomasz, et al. Oct. 24, 2000; Ohno, A., et al., Nippon Rinsho (2001) 59(4):673-680).

The lack of efficient screening systems in certain organisms can seriously impair efforts to screen candidate drugs. In part due to the increasing numbers of immunocompromised patients, infections with drug-resistant organisms and systemic fungal infections with normally benign organisms are on the rise, for example, many such infections are due to the normal human flora *Candida albicans*. *Candida* species are now the fourth most common cause of nosocomial bloodstream infections (Edmond et al. (1999) *Clin Infect Dis.* 29(2):239-44). Commensurate with the increase in the number of people contracting serious *Candida* infections, is an increase in the incidence of strains resistant to antifungal compounds (White, Marr, et al., (1998) *Clin Microbiol Rev* 11(2):382-402). To counteract this, new classes of antifungal compounds and their possible targets must be investigated.

The study in *Candida albicans* of new targets amenable to antifungal attack, using genetic approaches, has been hampered by several factors. First, the plasmids used with *Candida albicans* are usually present in cells as tandem copies and are quickly lost without selective pressure (Cannon et al. (1992) *Mol Gen Genet.* 235(2-3):453-457; Kurtz et al. (1987) *Mol Cell Biol.* 7(1):209-17; Pla et al. (1995) *Gene* 165(1): 115-20). Further, unlike *Saccharomyces cerevisiae*, no centromeric sequence or autonomously replicating sequence has been cloned which would allow episomal plasmids to be maintained without any selection.

Another factor that has hampered the study of *C. albicans* and the generation of effective treatments that this organism was thought to be diploid throughout its life cycle. Only recently has it been shown that *Candida* can be forced to mate (Magee (2000) *Science* 289(5477):310-313; Hull et al. (2000) *Science* 289(5477):307-310), possibly going through a tetraploid state. The presence of genetic elements akin to the mating alleles of S. cerevisiae suggests that meiotic division may lead to haploid cells, however such haploid isolates have not been observed. Accordingly, to study a new antifungal target, both chromosomal copies of the candidate gene must be inactivated see its effect on the cell. To knock out both copies, a construct called a "ura blaster" was developed (Alani (1987) *Genetics* 117(1):5-12; Fonzi et al. (1993) *Genetics* 134(3):717-28). Cells must be made auxotrophic for URA3, and creating an auxotrophic strain from a clinical isolate usually reduces virulence significantly or totally abolishes it (Lay et al. (1998) *Infect Immun.* 66(11):5301-6; Kirsch et al. (1991) *Infect Immun.* 59(9):3297-300; Polak (1992)

*Mycoses* 35(1-2):9-16; Cole (1995) *FEMS Microbiol Lett.* 126(2):177-80). A study has shown that even in virulent strains, recovery of URA3 function may not necessarily restore virulence to wild type levels (Lay et al. (1998), supra).

A third issue is that very few heterologous genes have been expressed in *C. albicans* due to its abnormal codon usage (CTG coding for serine instead of leucine) (Leuker (1994) *Mol Gen Genet.* 245(2):212-7). In order for a heterologous gene to be functionally expressed in *Candida albicans*, every CTG codon in the gene must be mutated to other leucine codons (Morschhauser et al. (1998) *Mol Gen Genet.* 257(4): 412-20). Thus, these and other difficulties have limited the study of *Candida* genes to strains in which URA3 or another nutritional marker has been knocked out. Many reporter genes are not used due to the effort needed to mutagenize them for expression.

Methods described in U.S. Pat. No. 5,650,135, make possible the detection of bioluminescent bacteria in a living animal without dissecting or otherwise opening the animal up ("in vivo monitoring")—the light is detected through muscle, skin, fur & other traditionally "opaque" tissues using a highly sensitive camera. Although green fluorescent protein (GFP) has been expressed in *C. albicans* (Cormack, Bertram, et al., (1997) *Microbiology* 143(Pt 2):303-11; Morschhauser, Michel, et al., (1998) *Mol Gen Genet* 257(4):412-20), GFP producing *C. albicans* cells have not yet been imaged inside a living animal. Srikantha, et al., ((1996) *J Bacteriol.* 178(1): 121-9) reported expression of the luciferase of the sea pansy *Renilla reniformis* in *C. albicans*, but the cost of the substrate, coelentrazine, makes it impractical for use in living animals.

In addition to *C. albicans* many other pathogenic organisms have become resistant to most or all antibiotics, thus making transformation of these organisms difficult, if not impossible by classical methods of introducing DNA comprising a drug resistance gene and selecting for drug resistance conferred by the DNA used for transformation.

Thus, there remains a need for methods of detecting transformation of target cells, particularly methods that do not involve selectable markers. The present invention provides, inter alia, such methods, expression cassettes, transposon cassettes and other tools useful for generating light-producing organisms, for example, pathogenic organisms (such as, MRSA, antibiotic-resistant bacteria, and *Candida albicans*) which are suitable for studies relating to infection and/or pathogenesis in vitro and in whole animals.

SUMMARY OF THE INVENTION

The present invention relates to methods for introducing a polynucleotide of interest into cells wherein no selectable marker is used, rather a screen for light production is used to identify cells comprising the polynucleotide of interest. The present invention also relates to cells produced by the methods of the present invention, as well as uses of such cells. In one embodiment of the present invention, the cells are antibiotic resistant bacteria, e.g., methicillin-resistant strains of *Staphylococcus aureus*, and vancomycin-resistant enterococci (VRE) strains, transformed by the methods of the present invention.

One aspect of the present invention is a method of introducing a polynucleotide into a cell, that is, a method of transforming a target cell. In this method a population of cells is provided. The population of cells is treated with a polynucleotide of interest under conditions that facilitate the uptake of the polynucleotide by at least a subpopulation of the cells. The polynucleotide of interest comprises a light generating protein coding sequence. In preferred embodiments the light generating protein coding sequence encodes a bioluminescent protein, e.g., a luciferase. Numerous methods for the introduction of polynucleotides into a target cell may be employed, including, but not limited to, the following: lipid-mediated transfer (e.g., using liposomes, including neutral and cationic lipids), direct injection (e.g., microinjection), cell fusion, microprojectile bombardment (e.g., biolistic methods, such as DNA particle bombardment), co-precipitation (e.g., with calcium phosphate, or lithium acetate), DEAE-dextran- or polyethylene glycol-mediated transfer, and viral vector-mediated transfer. The population of cells is then screened for a subpopulation of cells that have taken up the polynucleotide of interest. These cells are identified by their ability to express the light generating protein coding sequences which comprise the polynucleotide of interest. Light producing cells are isolated. These light producing cells are cells into which the polynucleotide has been introduced, i.e., transformed cells. Such light producing cells are then isolated to provide substantially pure colonies (i.e., clones) of light-producing cells, for example, by dilution or streaking for single colonies.

The polynucleotide used in the transformation method of the present invention comprises coding sequences for a light generating protein. Such a light generating protein may be, for example, a bioluminescent or fluorescent protein. In one embodiment of the present invention, the bioluminescent protein is a luciferase (e.g., encoded by luc or lux sequences).

Any transformable cell may be used in the practice of the present invention. Typically such cells do not emit light before transformation, although if a cell already produces light of a given wavelength, then a light generating protein coding sequence which produce a protein producing a different, identifiable wavelength of light may be used to transform such cells. Cells which can be employed in the methods of the present invention include, but are not limited to, procaryotic cells (e.g., gram-positive, gram-negative bacteria, as well as other procaryotes), and eucaryotic cells (e.g., yeast, such as *Candida* or *Saccharomyces*; plant cells; animal cells; tumor cells; tissue-specific cells). Insect cells may also be used in the methods of the present invention. In one aspect of the present invention, the population of cells comprises antibiotic-resistant bacteria, for example, methicillin-resistant strains of *Staphylococcus aureus*, and vancomycin-resistant enterococci (VRE) strains. The target cells, after treatment with the polynucleotide under conditions which facilitate uptake of the polynucleotide, are plated at an appropriate screening density based on the cell type and the kind of media (e.g., liquid or solid) on which the cells are being screened for the production of light.

In one embodiment of the present invention, the polynucleotide introduced into the cell comprises a promoterless polynucleotide sequence encoding a light generating protein. Typically, such a polynucleotide sequence is expressed after integration into the genome of the target organism, for example, adjacent an endogenous promoter in the genome of the target organism. A number of vectors may comprise such polynucleotides including, but not limited to integrating vectors, transposons (or other mobile genetic elements, such as, TY or mariner).

In another aspect, the polynucleotide introduced into the target cell comprises a promoter operably linked to the polynucleotide sequences encoding a light generating protein. A number of vectors may comprise such promoter-containing polynucleotide sequences including, but not limited to integrating vectors, transposons (or other mobile genetic elements, such as, TY or mariner), replicating plasmids, non-replicating plasmids, and the like. Plasmids may comprise, for example, shuttle vector sequences that allow passaging in a cell type in order to prepare a sufficient amount of polynucleotide to be used in transformation of the target cell. The promoters used in such constructs are functional in the target cells.

The light generating protein coding sequences are used to screen for transformed cells and, accordingly, other sequences of interest can be associated with the light generating protein coding sequences (e.g., in the same vector construct). The other sequences of interest may be associated with the same set of control elements used to express the light generating protein or, alternately, expression of such sequences of interest may be mediated by independent control elements associated with the sequence(s) of interest. For example, expression of the light generating protein coding sequences may be mediated by a first promoter and expression of further sequences of interest may be mediated by at least a second promoter.

In one aspect of the present invention, yeast is transformed by the methods described herein. Yeast transformations, for example of *Candida* cells, may be plated on a medium that enhances light production, for example, screening of the transformed population of cells may be carried out by plating the cells on SD rather than YPD plates (e.g., SD-ura plates supplemented with 50 µg/ml uridine, containing 600 µg/ml luciferin). Yeast cells, as well as other types of cells, may be plated at a variety of densities for initial screening, for example, at a density of approximately $2.5 \times 10^5$ cells/140 mm plate. In one embodiment of the present invention, screening takes place on a plate of solid medium. Isolation of the transformed cells may be carried out a number of ways including, picking samples of cells from a region of the plate of solid medium comprising cells producing light, inoculating the samples into liquid cultures, growing the cells in liquid cultures, evaluating aliquots of each liquid culture for light production, identifying liquid cultures comprising cells producing light, diluting and plating liquid cultures to obtain isolated single cells producing light, and identifying single colonies derived from single cells producing light.

Accordingly, the present invention provides methods of screening for transformed cells in a population of cells, wherein the method comprises, for example, providing a population of cells, wherein said cells are incapable of producing light, transforming the population of cells with a polynucleotide comprising a light generating protein coding sequence, and screening the transformed population of cells for cells producing light, wherein said cells that produce light are transformed cells. The present invention also includes transformed cells generated by the methods of the present invention and uses thereof.

These and other embodiments of the present invention will readily occur to those of ordinary skill in the art in view of the disclosure herein.

BRIEF DESCRIPTION OF THE FIGURES

FIG. 1 presents the complimentary oligonucleotide pairs used for site directed mutagenesis of luciferase for expression of the coding sequence in *Candida albicans*.

FIGS. 2A and 2B present oligonucleotides used to create a luciferase expression vector for use in the transformation of *Candida albicans*. FIG. 2C presents an alignment of synthetic linker A (SEQ ID NO:34) and synthetic linker B (SEQ ID NO:35).

FIG. 3B also shows the 5' to 3' sequences of the sense (SEQ ID NO:34) and antisense (SEQ ID NO:35) strands the NX linker.

DETAILED DESCRIPTION OF THE INVENTION

Figure 3A:
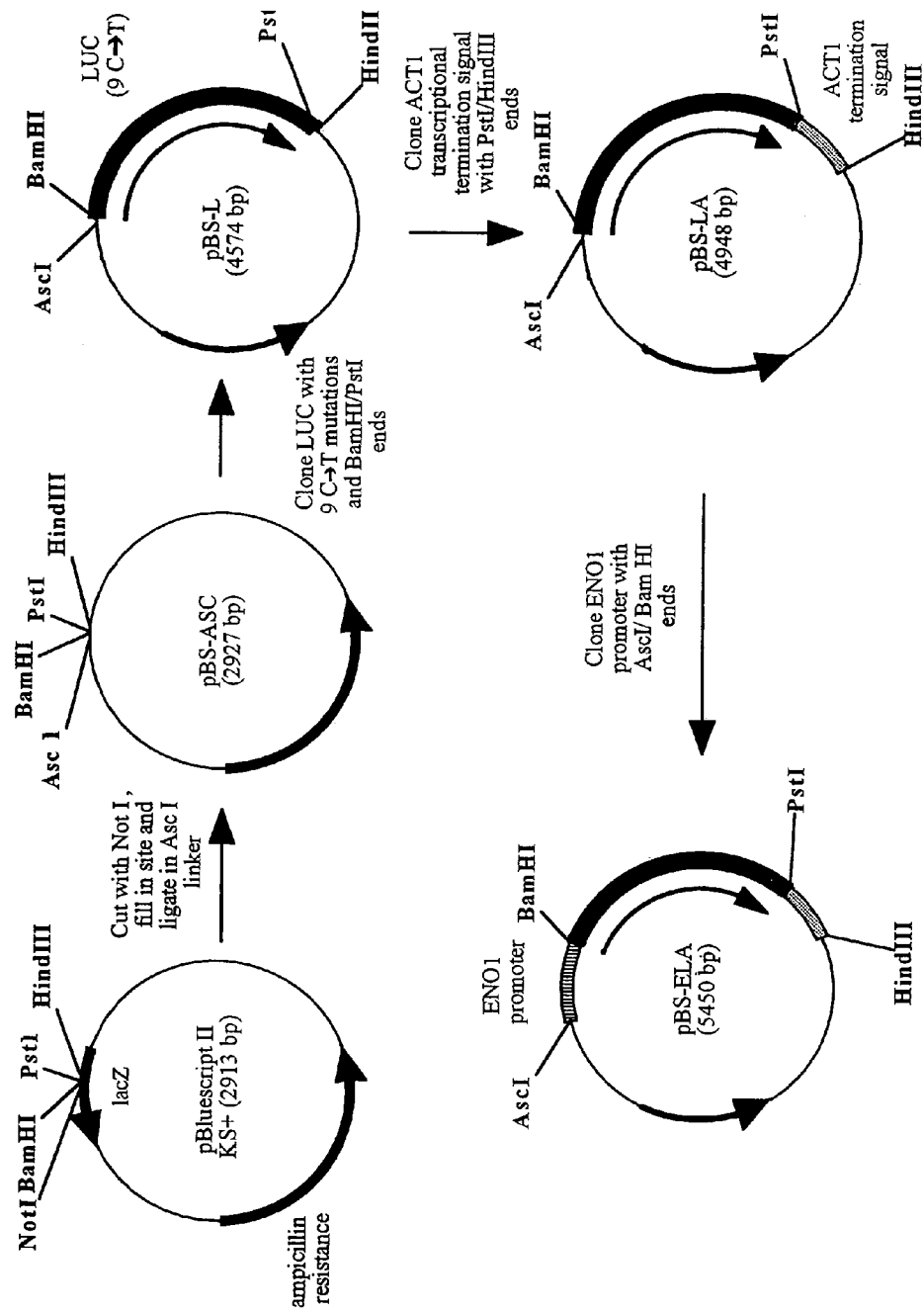
FIGS. 3A, 3B, and 3C graphically represent construction of the pGTV-ENO plasmid vector.

The practice of the present invention will employ, unless otherwise indicated, conventional techniques of chemistry, biochemistry, molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY (John Wiley and Sons, Inc., Media, Pa. (1995)); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entireties.

DEFINITIONS

In describing the present invention, the following terms will be employed, and are intended to be defined as indicated below. Unless otherwise indicated, all terms used herein have the same meaning as they would to one skilled in the art of the present invention.

As used in this specification and the appended claims, the singular forms "a," "an" and "the" include plural references unless the context clearly dictates otherwise. Thus, for example, reference to "an antigen" includes a mixture of two or more such agents.

The terms "transformation," "transformation method," and "method of transforming cells" refer to the transfer or introduction of a nucleic acid molecule(s), e.g., a vector construct, into a target cell such that the target cell, after transformation, comprises the nucleic acid molecule(s). Typically transformation methods are applied to a population of cells wherein a subpopulation of the cells ultimately comprise the nucleic acid molecule(s). Cells of the subpopulation which comprise the introduced nucleic acid molecule(s) are typically identified by, for example, a selection (e.g., ability to grow on a selective medium) or a screen (e.g., expression of a phenotype that allows the identification of cells comprising the introduced nucleic acid versus cells that do not contain the introduced nucleic acid). A "transformant" is a cell (e.g., "transformed cell") or organism that has generated by transformation. Such an introduction of a nucleic acid molecule(s) into a cell may be referred to as "genetic transformation" in order to distinguish it from "cellular transformation." Cellular transformation refers to the conversion of a normal cell to a neoplastic (or tumor) cell which typically occurs as the result of events under the control of different classes of oncogenes. Unless specifically indicated otherwise, the term "transformation" as used herein refers to genetic transformation, i.e., the introduction of nucleic acid molecule(s) into a target cell.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide when placed under the control of appropriate regulatory sequences (or "control elements") in a host system. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral, eucaryotic, or procaryotic DNA, and even synthetic DNA sequences. A transcription termination sequence may be located 3' to the coding sequence.

Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgamo (ribosome binding site) sequences, and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

A double-stranded DNA molecule comprises two strands of DNA having "opposite orientations," one strand being designated 5' to 3'; the second strand being its complement. Thus, a first coding sequence in a first strand and a second coding sequence in the complementary strand have "opposite" orientations relative to each other, that is, the first and second coding sequences are in opposite orientations relative to each other.

An "isolated polynucleotide" molecule is a nucleic acid molecule separate and discrete from the whole organism with which the molecule is found in nature. Such an isolated polynucleotide may be devoid, in whole or part, of sequences normally associated with it in nature.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics.

"Operably linked" refers to an arrangement of elements wherein the components so described are configured so as to perform their usual function. Thus, a given promoter that is operably linked to a coding sequence (e.g., a reporter gene) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant polynucleotide" as used herein describes a nucleic acid molecule obtained using the techniques of molecular biology, for example, by cloning, PCR amplification, plasmid isolation, use of expression systems, etc. The term "recombinant" as used with respect to a protein or polypeptide means a polypeptide produced by expression of a recombinant polynucleotide.

"Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transformed. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.). A preferred method of establishing percent identity in the context of the present invention is to use the MPSRCH package of programs copyrighted by the University of Edinburgh, developed by John F.

Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences is generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet A "gene" refers to a polynucleotide containing at least one open reading frame that is capable of encoding a particular product (e.g., a polypeptide, protein or RNA). Typically, the term "gene" includes control sequences associated with the expression of the product. The term "gene locus" refers to the physical position of a gene in the genome of an organism. Any of the polynucleotide sequences described herein may be used to identify larger fragments or full-length coding sequences of the genes with which they are associated. Methods of isolating larger fragment sequences are known to those of skill in the art.

The degree of sequence relatedness between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A nucleic acid comprising a defined sequence of contiguous nucleic acids "encodes" a corresponding polypeptide or RNA product. For example, a DNA sequence comprising an open reading frame encodes the polypeptide whose sequence corresponds to the open reading frame. As another example a DNA sequence can encode a corresponding rRNA, tRNA or mRNA sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring gene sequences to target cells (e.g., viral vectors, non-viral vectors, particulate carriers, and liposomes). Typically, a "vector construct" refers to a nucleic acid vector capable of transferring sequences of interest into target cells. Nucleic acid vectors can be transiently present in or capable of replication in target cells. Transient vectors typically do not have an origin of replication that can function in the target cell, or one which does not function under certain conditions in the target cell (a "conditional" origin of replication).

"Nucleic acid expression vector" refers to an assembly which is capable of directing the expression of a sequence or gene of interest. The nucleic acid expression vector includes a promoter which is operably linked to the sequences or gene(s) of interest. Other control elements may be present as well. For example, in addition to the components of an expression cassette, the plasmid construct may also include one or more bacterial origin(s) of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct which contains polynucleotide gene(s) or sequence(s) capable of being expressed in a cell. Expression cassettes may contain, in addition to polynucleotide gene(s) or sequence(s) of interest, additional transcriptional, translational or other regulatory or control elements. Such cassettes are typically constructed into a "vector," "vector construct," or "expression vector," (i.e., a "nucleic acid expression vector") in order to transfer the expression cassette into target cells.

A "transposon" as used herein defines a polynucleotide which comprises a repeated element capable of relocating from one genetic locus to another (e.g., from a chromosomal point to another chromosomal point, or from an episomal point to a chromosomal point), i.e., a transposon is a mobile genetic element. In a preferred embodiment of the present invention, a "transposon cassette" comprises a minimum unit required for transposition (e.g., first and second transposon inverted repeat sequences flanking an internal polynucleotide sequence comprising at least a transposase capable of inducing transposition mediated by said transposon inverted repeats). Alternately, a transposon cassette may be first and second transposon inverted repeat sequences flanking an internal polynucleotide sequence, where the transposase function is provided in trans or is encoded external to the transposon cassette (i.e., outside of the two transposon inverted repeats flanking the internal polynucleotide sequence). As used herein, a transposon cassette comprises at least two inverted repeat sequences flanking an internal region. The internal region may contain transposase coding sequence and/or other sequences of interest. A schematic representation of a transposon cassette is as follows: IR-internal region-IR, where IR represents the inverted repeats. In another embodiment, a representation is as follows: IR-tnp-IR, where tnp represents a transposase gene. Further, IR—sequence of interest—tnp-IR represents yet another embodiment, capable of inducing transposition mediated by the IR sequences. Further sequences, 5' and 3' of the inverted repeats may be included in the transposon cassette where indicated. A transposon cassette that is "functional" in a host organism is one that is capable of undergoing transposition in that organism. The term "transposant" typically refers to a cell in which a transposon has integrated into the cell's genome.

A "light generating protein" or "light-emitting protein" is a bioluminescent or fluorescent protein capable of producing light typically in the range of 200 nm to 1100 nm, preferably in the visible spectrum (i.e., between approximately 400 nm and 750 nm). Bioluminescent proteins produce light through a chemical reaction (typically requiring a substrate, energy source, and oxygen). Fluorescent proteins produce light through the absorption and re-emission of radiation (such as with green fluorescent protein). Examples of bioluminescent proteins include, but are not limited to, the following: "luciferase," unless stated otherwise, includes procaryotic (e.g., bacterial lux-encoded) and eucaryotic (e.g., firefly luc-encoded, or Renilla luciferase) luciferases, as well as variants possessing varied or altered optical properties, such as luciferases that produce different colors of light (e.g., Kajiyama, N., and Nakano, E., Protein Engineering 4(6):691-693 (1991)); and "photoproteins," for example, calcium activated photoproteins (e.g., Lewis, J. C., et al., Fresenius J. Anal. Chem. 366(6-7):760-768 (2000)). Examples of fluorescent proteins include, but are not limited to, green, yellow, cyan, blue, and red fluorescent proteins (e.g., Hadjantonakis, A. K., et al., Histochem. Cell Biol. 115(1):49-58 (2001)).

"Light-generating protein substrate" or "light-emitting protein substrate" describes a substrate of a light-generating protein, e.g., luciferase enzyme, that generates an energetically decayed substrate (e.g., luciferin) and a photon of light typically with the addition of an energy source, such as ATP or $FMNH_2$, and oxygen. Examples of such substrates include, but are not limited to, decanal in the bacterial lux system, 4,5-dihydro-2-(6-hydroxy-2-benzothiazolyl)-4-thiazolecarboxylic acid (or simply called luciferin) in the Firefly luciferase (luc) system, "panal" in the bioluminescent fungus Panellus stipticus system (Tetrahedron 44:1597-1602, 1988) and N-iso-valeryl-3-aminopropanol in the earth worm Diplocardia longa system (Biochem. 15:1001-1004, 1976). In some systems, as described herein, aldehyde can be used as a substrate for the light-generating protein.

"Light" is defined herein, unless stated otherwise, as electromagnetic radiation having a wavelength of between about 200 nm (e.g., for UV-C) and about 1100 nm (e.g., infrared). The wavelength of visible light ranges between approximately 400 nm to approximately 750 nm (i.e., between about 4,000 angstroms and about 7,500 angstroms).

"Animal" typically refers to a non-human animal, including, without limitation, farm animals such as cattle, sheep, pigs, goats and horses; domestic mammals such as dogs and cats; laboratory animals including ferrets, hares and rabbits, rodents, such as mice, rats, hamsters, gerbils, and guinea pigs; non-human primates, including chimpanzees. The term "animal" may also include, without limitation; birds, including domestic, wild and game birds such as chickens, turkeys and other gallinaceous birds, ducks, geese, and the like, as well as amphibians, fish, insects, reptiles, etc. The term does not denote a particular age. Thus, adult, embryonic, fetal, and newborn individuals are intended to be covered.

A "transgenic animal" refers to a genetically engineered animal or offspring of genetically engineered animals. A transgenic animal usually contains material from at least one unrelated organism, such as from a virus, microorganism, plant, or other animal. The term "chimeric animal" is used to refer to animals in which the heterologous gene is found, or in which the heterologous gene is expressed in some but not all cells of the animal.

The term "selectable marker," as used herein, describes a coding sequence that confers on an organism transformed with the selectable marker coding sequence a growth advantage on a medium relative to the non-transformed organism. Examples of selectable markers include, but are not limited to, (i) the complementation of a mutant gene by a functional gene, for example, complementation of an auxotrophic mutation, such as use of the URA3 gene to complement ura3-mutants (such mutants are unable to grow in the absence or uridine or uracil), (ii) the introduction into a cell of a coding sequence that provides a dominant, selectable phenotype, for example, a sequence encoding a drug resistant ribosomal protein, and (iii) the introduction into a cell of a coding sequence that confers a resistance to a drug added to the medium, such as the beta-lactamase gene allowing growth of bacteria (E. coli) in media containing ampicillin. A selectable marker does not include a marker that confers a phenotype that must be scored by a non-growth-related assay, such as the ability to generate light. As used herein, colonies are "screened" for their ability to generate light.

"Analyte" as used herein refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

GENERAL OVERVIEW OF THE INVENTION

The compositions and methods of the present invention facilitate the ability to confer light-producing properties on an organism or cell of one's choice. Further, the compositions and methods of the present invention allow the introduction of any polynucleotide of interest into a target cell or organism using a sequence encoding a light-generating protein as a screenable marker to identify transformants of such target cells or organisms. The ability to use a light-generating protein as a screen for transformation of cells with a polynucleotide of interest eliminates the necessity for a selectable marker, for example, in difficult to transform cells or organisms. The sequences encoding the light-generating protein can be operably linked to any heterologous gene of interest and, accordingly, light production can serve as a reporter for successful transformation of a cell with the heterologous gene of interest.

One aspect of the present invention comprises a method of introducing a polynucleotide into a cell, that is, a method of transforming a target cell. In this method a population of cells is provided. The population of cells is treated with a polynucleotide of interest under conditions that facilitate the uptake of the polynucleotide by at least a subpopulation of the cells. The polynucleotide of interest comprises a light generating protein coding sequence. In one embodiment the light generating protein coding sequence encodes a bioluminescent protein, e.g., a luciferase. Numerous methods for the introduction of polynucleotides into a target cell may be employed, including, but not limited to, the following: lipid-mediated transfer (e.g., using liposomes, including neutral and cationic lipids), direct injection (e.g., microinjection), cell fusion, microprojectile bombardment (e.g., biolistic methods, such as DNA particle bombardment), co-precipitation (e.g., with calcium phosphate, or lithium acetate), DEAE-dextran- or polyethylene glycol-mediated transfer, and viral vector-mediated transfer. The population of cells is then screened for a subpopulation of cells that have taken up the polynucleotide of interest. These cells are identified by their ability to express the light generating protein coding sequences which comprise the polynucleotide of interest. Light producing cells are isolated. These light producing cells are cells into which the polynucleotide has been introduced, i.e., transformed cells. Such light producing cells are then isolated to provide substantially pure colonies (i.e., clones) of light-producing cells, for example, by dilution or streaking for single colonies.

Furthermore, organisms bearing such sequences encoding light generating proteins could, for example, be followed with in vivo monitoring in various models of infection or used in the tracking of infection and/or pathogenesis, e.g., in the food industries. In particular, it would be desirable to confer such light-producing properties on organisms that are resistant to any available selection method. For example, certain ubiquitous pathogens (e.g., *Candida albicans* and some species of *Staphylococcus*) are resistant to antibiotic or other common selectable markers. Other organisms which it would also be desirable to confer light-producing properties on organisms such as *Chlamydia, Treponema pallidum, Heliobacter pylori*, and other organisms which are difficult to manipulate and which have not previously been amenable to pharmaceutical intervention.

The present invention teaches the use of plasmids and expression cassettes (e.g., modified luciferase operons and transposon cassettes containing Tn4001, Tn917, and the like) to facilitate the genetic manipulation of organisms of interest, including, but not limited to, Gram-negative bacteria (including Heliobacter pylori and others); Gram-positive bacteria (including related organisms such as *Chlamydia* and *Treponema pallidum*) and eucaryotic organisms such as yeast (including *Candida albicans* and others).

In one aspect, the present invention relates to constructs containing a luciferase gene. In particular, the invention includes re-engineering a eucaryotic luciferase, for example a luciferase derived from *Photinus pyralis*. The re-engineering of these luciferase operon includes, for example, site-directed mutagenesis to alter (e.g., optimize) codon usage. Nucleic acid coding sequences encoding a chosen light-generating protein may be optimized for expression in a target organism by methods known in the art in view of the teachings of the present invention.

By way of example, it is known that in most eucaryotes, CTG codes for amino acid leucine while in *Candida*, CTG codes for the amino acid serine. In order for a heterologous gene to be expressed in *Candida*, it appears that the CTG codons in eucaryotic luciferase must be mutated to leucine-encoding sequences (e.g., TTG). The re-engineered luciferase operon can then be inserted into a vector comprising one or more of the following operably linked to the luciferase-encoding sequence: (1) a promoter(s) that is(are) active or highly transcribed in the target cell (e.g., *C. albicans* enolase (ENO1) promoter); (2) a polyadenylation signal (e.g., *C. albicans* actin (ACT1) polyadenylation signal); and (3) a heterologous gene of interest. In certain embodiments, the promoter(s) and/or polyadenylation signal(s) flank the luciferase operon.

In another aspect, the invention relates to the use of promoterless luciferase cassettes to transform organisms of interest to a light-producing phenotype by integrating the cassette into the genome of those organisms by means of a transposon, wherein the integration occurs adjacent an endogenous promoter in the target organism. For example, a promoterless luciferase (e.g., lux) cassette was inserted into the Tn4001 transposon, and cells of interest were then transformed with a shuttle vector carrying the Tn4001 luciferase construct. Transposition events subsequent to transformation resulted in integration of the luciferase cassette into the genome of the host organism and resulted in the ability of the organism to produce light; integration of the otherwise promoterless cassette behind an active promoter sequence yielded host organisms having a light-producing phenotype. Using this approach several different genera of Gram-positive bacteria were made brightly light-producing, either constitutively or inducibly.

The constructs described herein (e.g., modified luciferase plasmids and transposon constructs) can be inserted into a suitable backbone (e.g., a shuttle vector) and thereby confer the ability to produce the product of the coding sequence of interest (which, in the case of a light-generating protein, also confers the ability to produce light in a cell or animal) upon integration of the coding sequence of interest, (e.g., light-generating protein coding cassette) behind an active promoter region in the host cell genome. In one aspect, the constructs described herein allow for the generation of light-producing organisms (e.g., gram-positive bacteria) and the use of these organisms in animal models.

Many types of light-generating protein sequences are useful in the practice of the present invention and are typically optimized for expression in the target organism.

Thus, provided herein are methods of screening for introduction of nucleic acid (e.g., heterologous gene of interest) into target cells without the need for a selectable marker. This is particularly useful in pathogenic strains, such as Candida or resistant bacteria, where there is no available selectable marker. Target host cells are transformed with the constructs described herein to provide the opportunity for subsequent integration of the nucleic acids. The resulting light-producing phenotype, which may be constitutive, inducible or repressible depending on the properties of the promoter region behind which the transposon cassette, can then be used to detect successful transformations.

Such transformed cells may then be used, for example, to screen candidate effector molecules in vitro and in animal models. Cells (or colonies) that exhibit light production attributable to the activity of promoters induced by infection can be used to identify effective pharmaceutical agents. For example, cells which exhibit light production are used to infect experimental and control animals. The experimental animals are then treated with a pharmaceutical agent of interest. Both the experimental animals and the controls are monitored for light production, and effective agents identified as those which, for example, extinguish the ability to produce light.

Advantages of the present invention include, but are not limited to, (i) transforming a variety of organisms, including Gram-positive bacteria, antibiotic-resistant organisms, Candida, and the like; (ii) obtaining high levels of light generating protein expression in those transformed organisms, which, for example, permits more sensitive detection of light produced both in vitro and in vivo; (iii) integration of the cassette into the host chromosome such that the sequences encoding the light generating protein become operably linked to host cell promoters, which, for example, permits identification of promoters involved in pathogenesis; and stable light production from such organsims at physiological temperatures (e.g., 37° C.-42° C.).

Specific aspects of the methods and constructs of the present invention are discussed below.

1. Light-Generating Proteins

The practice of the present invention will typically employ nucleotide sequences encoding light generating proteins. When using the light generating reporter proteins described herein, expression can be evaluated accurately and non-invasively as previously described (see, for example, Contag, P. R., et al., (1998) Nature Med. 4:245-7; Contag, C. H., et al., (1997) Photochem Photobiol. 66:523-31; Contag, C. H., et al., (1995) Mol Microbiol. 18:593-603) and described herein.

In one aspect of the invention, the light generating protein is luciferase. Bioluminescence provides a powerful reporter system for studying bacterial infection (e.g., U.S. Pat. No. 5,650,135). Luciferase is a term applied to members of a family of diverse enzymes which share the property of producing light when provided with a substrate (e.g., luciferin, long-chain aldehyde or colentrazine), an energy source (e.g., ATP or $FMNH_2$) and oxygen. Luciferases can be broadly classified into eucaryotic luciferases (encoded by luc genes) and prokaryotic luciferases (encoded by lux genes). Eucaryotic luciferase ("luc") is typically encoded by a single gene (see, e.g., de Wet, J. R., et al., (1985), Proc. Natl. Acad. Sci. U.S.A. 82:7870-7873; de Wet, J. R., et al., (1987) Mol. Cell. Biol. 7:725-737).

Bacterial luciferase ("lux") is typically made up of two subunits (α and β) encoded by two different genes (luxA and luxB) on the lux operon. Three other genes on the operon (lux C, lux D and luxE) encode the enzymes required for biosynthesis of the aldehyde substrate. Bacterial lux is present in certain bioluminescent Gram-negative bacteria (e.g., Photorhabdus luminescens) and the wild-type operon is ordered CDABE.

In addition, another bacterial gene, luxY, isolated from Vibrio fischeri strain Y-1, encodes a yellow fluorescent protein (YFP), a substrate which emits yellow light with a lambda max of 545 nm when acted upon by the luciferase enzyme. See Baldwin, T. O., et al. (1990) Biochem 29:5509-5515.

In another aspect of the present invention, the light-generating protein is a fluorescent protein, for example, blue, cyan, green, yellow, and red fluorescent proteins.

Several light-generating protein coding sequences are commercially available, including, but not limited to, the following. Clontech (Palo Alto, Calif.) provides coding sequences for luciferase and a variety of fluorescent proteins, including, blue, cyan, green, yellow, and red fluorescent proteins. Enhanced green fluorescent protein (EGFP) variants are well expressed in mammalian systems and tend to exhibit brighter fluorescence than wild-type GFP. Enhanced fluorescent proteins include enhanced green fluorescent protein (EGFP), enhanced cyan fluorescent protein (ECFP), and enhanced yellow fluorescent protein (EYFP). Further, Clontech provides destabilized enhanced fluorescent proteins (dEFP) variants that feature rapid turn over rates. The shorter half life of the dEFP variants makes them useful in kinetic studies and as quantitative reporters. DsRed coding sequences are available from Clontech. DsRed is a red fluorescent protein useful in expression studies. Further, Fradkov, A. F., et. al., described a novel fluorescent protein from Discosoma coral and its mutants which possesses a unique far-red fluorescence (FEBS Lett. 479 (3), 127-130 (2000)) (mRNA sequence, GENBANK Accession No. AF272711, protein sequence, GENBANK Accession No. AAG16224). Promega (Madison, Wis.) also provides coding sequences for fire fly luciferase (for example, as contained in the pGL3 vectors). Further, coding sequences for a number of fluorescent proteins are available from GENBANK, for example, accession numbers AY015995, AF322221, AF080431, AF292560, AF292559, AF292558, AF292557, AF139645, U47298, U47297, AY015988, AY015994, and AF292556.

In addition, further light generating systems may be employed, for example, when evaluating expression in cells. Such systems include, but are not limited to, Luminescent beta-galactosidase Genetic Reporter System (Clontech).

1A. Lux-Encoding Cassettes

In one aspect of the invention, gene cassettes comprising polynucleotides encoding both the structural and substrate-encoding lux gene-products are provided. Experiments performed in support of the present invention have demonstrated that rearranging the lux genes, for example, from the wild-type CABDE to ABCDE, and inserting transcriptional and/or translational control sequences, which are chosen based on the target organism in which expression is desired, before one or more of the lux genes, confers on the resulting luciferase an enhanced ability to produce light. For example, when used in the transformation of Gram-positive bacteria, Gram-positive Shine-Dalgarno sequences are inserted upstream of the coding sequences. When used for the transformation of other organisms appropriate transcriptional and/or translational enhancement sequences may be employed (e.g., Kozak sequences in eucaryotic cells, Gram negative Shine-Dalgamo sequences for Gram negative organisms). In some organisms, for example, eucaryotes, each of the lux genes may be placed under the transcriptional control of a separate promoter. The luxABCDE cassettes express not only luciferase, but also the biosynthetic enzymes necessary for the synthesis of the lux luciferase's substrate—aldehyde. Accordingly, oxygen is the only extrinsic requirement for bioluminescence when such cassettes are used.

In another aspect of the invention, luxY may be added to a cassette comprising light generating protein coding sequences. For example, adding the luxY gene to the luxAB-CDE gene cassette results in broadening the range of wavelength of light emitted during bioluminescence towards the red end of the visible light spectrum. Given that longer-wavelength light more easily penetrates living tissue as compared to light of shorter wavelengths, selected embodiments of the luxABCDE gene cassette of the present invention will therefore additionally include the luxY coding sequence, as a means of increasing the sensitivity of applications which employ bioluminescence as a reporter means.

In one aspect, luxAB gene cassettes are provided. When used for the transformation of Gram positive organisms, the luxAB cassettes typically contain a Gram positive ribosome binding site (also referred to as a "Shine-Dalgarno" sequence) operably linked upstream of each of the polynucleotides encoding luxA and B. When used for the transformation of other organisms appropriate transcriptional and/or translational enhancement sequences may be employed (e.g., promoter sequences, Kozak sequences in eucaryotic cells, Gram negative Shine-Dalgarno sequences for Gram negative organisms). Host organisms carrying the luxAB cassette exhibit bioluminescence when provided with exogenous aldehyde substrate. LuxAB cassettes confer higher levels of luciferase activity than found in previously known constructs, particularly when expressed in Gram-positive bacteria such as *Stapholococcus* or *Streptococcus*.

The coding sequences of the lux encoded genes may be optimized for expression in a target organism. For example, given the sequence of a polypeptide product of a lux gene, appropriate codons can be chosen to encode the polypeptide where such codons are chosen based on the preferred codon usage in the target organism.

Modified lux coding sequences have also been described, e.g., WO 01/18195, published 15 Mar. 2001, Xenogen Corporation.

In alternative embodiments, the sequences producing two or more light-generating polypeptides producing emitted light at two or more wavelengths may be provided as the first sequence of interest in separate transposon cassettes; the transposon cassettes may in turn be provided in either a single vector backbone or in multiple vector backbones. Such constructs may be used to produce, for example, single microorganisms bearing multiple transposon cassettes of the present invention, where the transposon cassettes may each encode light generating polypeptides that emit light at different wavelengths.

1B. Luc-encoding Cassettes

The present invention also includes gene cassettes that allow for expression of eucaryotic luciferase in a target cell. As noted above, various eucaryotic luciferases have been identified and are commercially available, for example, plasmid pGL2 (Promega, Madison, Wis.) contains a *Photinus pyralis* luciferase.

A variety of luciferase encoding genes have been identified including, but not limited to, the following: B. A. Sherf and K. V. Wood, U.S. Pat. No. 5,670,356, issued 23 Sep. 1997; Kazami, J., et al., U.S. Pat. No. 5,604,123, issued 18 Feb. 1997; S. Zenno, et al, U.S. Pat. No. 5,618,722; K. V. Wood, U.S. Pat. No. 5,650,289, issued 22 Jul. 1997; K. V. Wood, U.S. Pat. No. 5,641,641, issued 24 Jun. 1997; N. Kajiyama and E. Nakano, U.S. Pat. No. 5,229,285, issued 20 Jul. 1993; M. J. Cormier and W. W. Lorenz, U.S. Pat. No. 5,292,658, issued 8 Mar. 1994; M. J. Cormier and W. W. Lorenz, U.S. Pat. No. 5,418,155, issued 23 May 1995; de Wet, J. R., et al, *Molec. Cell. Biol.* 7:725-737, 1987; Tatsumi, H. N., et al, *Biochim. Biophys. Acta* 1131:161-165, 1992; and Wood, K. V., et al, *Science* 244:700-702, 1989; all herein incorporated by reference. Another group of bioluminescent proteins includes light-generating proteins of the aequorin family (Prasher, D. C., et al., Biochem. 26:1326-1332 (1987)). Luciferases, as well as aequorin-like molecules, require a source of energy, such as ATP, NAD(P)H, and the like, and a substrate, such as luciferin or coelentrizine and oxygen.

Wild-type firefly luciferases typically have emission maxima at about 550 nm. Numerous variants with distinct emission maxima have also been studied. For example, Kajiyama and Nakano (*Protein Eng.* 4(6):691-693, 1991; U.S. Pat. No. 5,330,906, issued 19 Jul. 1994, herein incorporated by reference) teach five variant firefly luciferases generated by single amino acid changes to the *Luciola cruciata* luciferase coding sequence. The variants have emission peaks of 558 nm, 595 nm, 607 nm, 609 nm and 612 nm. A yellow-green luciferase with an emission peak of about 540 nm is commercially available from Promega, Madison, Wis. under the name pGL3. A red luciferase with an emission peak of about 610 nm is described, for example, in Contag et al. (1998) *Nat. Med.* 4:245-247 and Kajiyama et al. (1991) *Port. Eng.* 4:691-693. The coding sequence of a luciferase derived from *Renilla muelleri* has also been described (mRNA, GENBANK Accession No. AY015988, protein Accession AAG54094).

In the constructs and methods described herein, a eucaryotic luciferase is preferably modified so that codon usage reflects those codons more often used in the target cell. Codon modification can be achieved, for example, by utilizing the Codon Usage Database, available on the World Wide Web. For example, in Candida the codon CTG is expressed as a serine residue, while in many other eucaryotes (including *P. pyralis*), CTG is expressed as a leucine residue. Accordingly, it is preferred that CTG codons in the *P. pyralis* be modified to TTG (or any other codon that is expressed as leucine in *Candida*).

A preferred method of site-specifically mutating a luciferase operon is by using PCR. General procedures for PCR as taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers (e.g., oligonucleotide primers) are described below in the Examples. After amplification, the resulting fragments can be detected by agarose gel electrophoresis followed by visualization with ethidium bromide staining and ultraviolet illumination. Site-specific mutagenesis is also described below in the Examples and FIG. 1 shows oligonucleotide pairs used for site-directed mutagenesis of *P. pyralis*. Preferably, the changes do not affect the amino acid sequence of the resulting protein.

Another method for obtaining a modified luciferase is random mutagenesis to randomly alter the amino acids, followed by screening for clones exhibiting efficient luminescence. Random mutagenesis can be performed, for example, by generating oligonucleotide(s) to randomly alter the target DNA sequence.

2. Vectors

The sequences encoding light generating proteins can then be used to construct vectors for use in the transformation of a target cell. Several such constructs are described in the Examples. Vectors for use in the present invention can generally be divided into two groups, promoter-less constructs and promoter containing constructs.

In certain embodiments, the constructs will be promoterless (e.g., transposon shuttle vectors detailed below). In other embodiments, however, the construct will include a promoter sequence operably linked to the luciferase sequence. Preferably, the promoter is active in the target cell. Promoters functional in a target organism may be identified by examining the prior art associated with the target organism (e.g., as exemplified below for *Candida*). Similarly, further transcriptional and/or translational control elements are preferably derived from the target organism.

Constructs without a promoter associated with the light generating protein coding sequences are useful for transformation vectors when integration into the genome of the target organism is desired. In this situation, expression of the light generating protein and subsequent light production is dependent on the integration of the light generating protein coding sequences adjacent an endogenous, active promoter. Vector constructs containing such promoterless light generating protein coding sequences may be linear or circular. They may include sequences to target integration at a specific genomic location(s), such integration may be mediated by site specific integration (e.g., a single crossover event with a homologous sequence in a circular vector; or a homologous recombination where two crossover events occur to essentially replace a genomic segment). Alternatively, linear or circular polynucleotides may be introduced that randomly integrate into the genome. Such promoterless constructs may comprise additional elements, including, but not limited to, those described below.

In another embodiment, the present invention employs vector constructs where the light generating protein coding sequences are under the transcriptional control of a chosen promoter (i.e., a promoter containing construct). As described above for promoterless constructs, promoter containing constructs may be linear or circular and they may contain elements that direct integration to one or more sites, or such vectors may be introduced into target cells and random integration exploited to obtain transformants.

Thus, the light generating protein encoding sequences described herein can be inserted into vectors promoterless or promoter containing vectors that further comprise one or more of the following: (1) one or more polyadenylation signals, (2) one or more integration targeting sequences, (3) one or more origins of replication, (4) one or more transcription termination elements, and (5) one or more coding sequences of interest. The coding sequences of interest typically comprise their own transcriptional and/or translational control elements. For example, if a promoterless light generating protein construct is used and a promoter functional in the target organism is operably linked to a coding sequence of interest, the vector may further comprise transcription termination sequences to prevent read-through transcription of the light generating protein encoding sequences from the transcription control element associated with the coding sequence of interest. In another exemplary embodiment, for example when transforming Gram positive bacteria, promoterless coding sequences of interest may be in tandem with promoterless light generating protein coding sequences, wherein the coding sequences of interest include operatively linked Gram positive Shine and Dalgarno sequences to create, essentially, sequences that provide a polycistronic message.

In one aspect of the present invention the promoterless constructs comprise a transposable or mobile genetic element.

2A. Transposable or Mobile Genetic Elements

In one aspect, the practice of the present invention employs the use a transposable or mobile genetic element. The specific transposable or mobile element is chosen based on the target organism. Exemplary target organisms and associated transposable or mobile elements include, but are not limited to, the following: bacteria (e.g., gram-positive, gram-negative), yeast (e.g., *Saccharomyces cerevisiae* Ty elements, Boeke, Garfinkel et al. (1985) *Cell* 40(3): 491-500), plants (e.g., maize), and insects (e.g., mariner in *Drosophila*). For use in the present invention, the transposon or mobile genetic element is modified to include either a promoterless light generating protein construct or a promoter containing light generating protein construct. The transposon or mobile genetic element may be modified to further include other elements, such as additional polynucleotide sequences of interest. Typically, all components added to the transposon or mobile genetic element are included between the boundaries of the functional transposon or mobile genetic element, e.g., inverted repeats, such that when the transposon or mobile genetic element relocated the added components move with the transposon or mobile genetic element.

One exemplary transposon for use in the present invention is Tn4001, a class I composite-type transposon originally isolated from *Staphyloccus aureus* (GeneBank Accession No. M18086, base pair 1-1,324 of the sequence; see Byrne, M. E., Rouch, D. A., and Skurray, R. A. (1989) *Gene* 81:361-367). This element is capable of inserting with a high degree of randomness into the bacterial chromosome of Gram-positive organisms. Experiments performed in support of the present invention indicate that the transposon functions in Gram-negative host cells as well.

The components of the Tn4001 transposon include (1) two identical copies of the IS256 insertion sequence, present as inverted repeats (IR's) which define an insertion sequence therebetween, and (2) a transposase gene located within the inverted repeats, which defines an insertion. Generally, when referring to the transposon the inverted repeats are considered to be the boundary of a functional transposon unit. This basic structure may be further modified and placed into a variety of vector backbones, as discussed below.

For example, additional sequences of interest may be inserted between the inverted repeats (e.g., 5'—IR—light generating protein coding sequences—sequence of interest—IR 3'), as well as the light generating protein coding sequences. In one embodiment, the additional sequences of interest lack an associated promoter region. In this case transcriptional enhancement sequences may be added between each protein coding sequence (i.e., to create a polycistronic message). In an alternative embodiment, a promoter functional in the target organism is operatively linked to the sequence of interest.

When promoterless constructs comprising the light generating protein coding sequences are used, the light generating protein coding sequences and any additional sequences of interest are preferably introduced into the Tn4001 transposon such that the direction of transcription for the inserted sequences is opposite that of the direction of the transposase coding sequence, and is therefore not under influence of transposase promoter. Hence, the sequences will not be transcribed unless and until integration of the insertion sequence behind an active or activatable promoter region occurs. As a corollary, this means that the coding sequences for the open reading frames for the sequences of interest and the transposase are in opposite orientations in the DNA. Alternately, the tranposase sequence may be present in the same orientation as the sequence of interest, provided that it is located downstream of that sequence, in order to avoid read-through from the endogenous transposase promoter and expression of the light generating protein gene product prior to integration.

When promoterless constructs are used in the practice of the present invention, the light-generating protein sequences are typically employed in the absence of a promoter contained within the tranposable element. That is, no promoter sequence is typically present within the transposon that can mediate transcription of the light-generating protein. In a preferred embodiment, the light-generating protein sequence is inserted adjacent or in close proximity to the 3' end of the 5' inverted repeat sequence, e.g., 5'-IR-light generating sequences-IR-3'. Further, the sequence is inserted in an orientation opposite that of the tranposase sequence, such that even with transcription of the transpose sequence there is no transcription of the sequence of interest (e.g., light-generating polypeptide coding sequences) prior to integration into the genome of an organism of interest adjacent an active host promoter region.

The transposon cassettes are typically cloned into shuttle vectors for ease of manipulation and isolation of large quantities of vector DNA. A number of such shuttle vectors are commonly available, e.g., pAUL-A (Chakraborty, et al. (1992) *J. Bacteriol.* 174:568-574); pE194 (Sozhamannan, s., et al. (1990) *J. Bacteriol.* 172: 4543-4548; see http://ph-age.atcc.orWvectors/gifs/68359.gif for a map of this vector; see ftp://ftp.atcc.org/pub/vector_segs/pE194.html for the full sequence); pMK4 (Sullivan, M., et al., (1984) *Gene* 29:21-26), pDL289 (Buckley, N., et al., (1995) *J. Bacteriol* 177: 5028-5034), pSK+ BLUESCRIPT (Stratagene, La Jolla, Calif.); and the pSUM series mycobacteria shuttle vector (Ainsa, J. A., et al., (1996) *Gene* 176:23-26). Similarly vector backbones can be chosen for any given transposon or mobile genetic element based on the host (i.e., target) cell into which the transposon or mobile genetic element is to be introduced.

For TN4001, such vector backbones may comprise, (1) a Gram negative origin of replication (may be conditional, e.g., temperature-sensitive), (2) a Gram-positive origin of replication (may be conditional, e.g., temperature-sensitive), (3) a polylinker region, and (4) transcription termination regions.

Example 1 describes the construction of an exemplary transposable element of the present invention, the transposon comprising promoterless light generating protein coding sequences. Example 2 describes the introduction of the transposon into a number of vectors useful for introducing the transposon into a number of different bacteria. Example 3 describes use of one of the vector/transposon constructs to obtain transformed, bioluminescent colonies. Cells transformed by the method of the present invention were isolated from among colonies plated at high density on solid medium using optical detection and manual isolation.

In one aspect of the present invention, vector backbones possess transcription termination sequences flanking one or both sides of the transposon or mobile genetic element, for the purpose of preventing expression of the light generating polypeptide prior to integration of the cassette into the host organism's DNA. Such regions are known in the art. See e.g., Henkin, T. M., (1996) *Ann Rev Genet* 30:35-37; MacDonald L. E., et al. (1993) *J. Mol. Biol.* 232:1030-1037; Jeng, S. T., et al. (1997) *Can J Microbiol* 43:1147-1156.

In the preferred embodiment where the origin of replication is functional in both Gram-negative and Gram-positive organisms, the presence of a Gram-negative origin of replication permits replication of the vector in Gram-negative organisms, thereby facilitating manipulation of the inserted sequences while avoiding the restriction endonuclease systems of Gram-positive host organisms, as well as permitting isolation of large quantities of vector construct DNA. In this case, a selectable marker may be included in the vector to facilitate passage in the gram-negative organism, where the resulting DNA is to be used for transformation of the gram-positive organism. Selectable markers are employed for passaging vectors in a host organism in order to obtain a quantity of DNA. In this aspect of the present invention, selectable markers are not used to identify transposants, rather expression in a target cell of the light generating protein sequences is the screen used to identify transposants.

Alternatively, an origin of replication may be employed that is functional in both Gram-positive and Gram-negative organisms, e.g., the origins of replication present in certain Streptomyces plasmids (such as, pCK1).

The origin of replication in the vector carrying the transposon or mobile genetic element may be either continuously active or may instead be conditional, e.g., the temperature-sensitive origin from pE194, as is found in the pAUL-A shuttle vector. An advantage of including a conditional origin of replication in the vector constructs of the present invention is that such elements permit stabilization of the vector construct in the host organism of interest grown under permissive conditions, while permitting the host organism to be "cured" of the vector when grown under restrictive conditions (e.g., temperature elevated to a non-permissive level after transposition has occurred).

Accordingly, after transformation of the target organism with the vector containing the transposon or mobile genetic element (which comprises either promoter containing or promoterless sequences encoding a light generating protein) transformants are identified by their ability to produce light. Typically, after a transformation protocol cells are plated and regions of the plate containing light generating cells are identified. These areas are then passaged to provide more pure cultures of the transformed cells expressing the light generating protein coding sequences. Such manipulations can be carried out in liquid or semi-solid culture materials as well, employing, for example, microtiter plates.

2B. Vectors and Plasmids

The methods of the presents invention can be used for the transformation of a variety of cell types using appropriate expression vectors comprising chosen expression control elements. Appropriate vectors and control elements for any given cell type can be chosen by one having ordinary skill in the art in view of the teachings of the present specification and information known in the art of expression vectors.

For example, light generating protein coding sequences can be inserted into a vector which includes control elements operably linked to the coding sequence, which allow for the expression of the gene in a chosen cell-type. Exemplary promoters for use in mammalian cell expression include, but are not limited to, the SV40 early promoter, a CMV promoters, HIV-LTR, the mouse mammary tumor virus LTR promoter (MMLV-LTR), FIV-LTR, the adenovirus major late promoter (Ad MLP), and the herpes simplex virus promoter. Other nonviral promoters, such as a promoter derived from the murine metallothionein gene, may also be used for mammalian expression. Typically, transcription termination and polyadenylation sequences are also present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., *Nuc. Acids Res.* (1991) 19:3979-3986).

Enhancer elements may be used to increase expression levels of mammalian vector constructs. Exemplary enhancers include, but are not limited to, the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence (Chapman et al., *Nuc. Acids Res.* (1991) 19:3979-3986).

Suitable prokaryotic vectors include, for example, plasmids such as those capable of replication in *E. coli* (for example, pBR322, ColE 1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)) and many such vectors are commercially available. Bacillus plasmids include pC194, pC221, pT127, and the like, and are disclosed by Gryczan (In: The Molecular Biology of the Bacilli, Academic Press, NY (1982), pp. 307-329). Suitable Streptomyces plasmids include pli101 (Kendall et al., J. Bacteriol. 169:4177-4183, 1987), and streptomyces bacteriophages such as □C31 (Chater et al., In: Sixth International Symposium on Actinomycetales Biology, Akademiai Kaido, Budapest, Hungary (1986), pp. 45-54). Pseudomonas plasmids are reviewed by John et al. (Rev. Infect. Dis. 8:693-704, 1986), and Izaki (Jpn. J. Bacteriol. 33:729-742, 1978).

Suitable eucaryotic plasmids include, for example, BPV, EBV, vaccinia, SV40, 2-micron circle, pcDNA3.1, pcDNA3.1/GS, pYES2/GS, pMT, p IND, pIND(Spl), pVgRXR (Invitrogen), and the like, or their derivatives. Such plasmids are well known in the art (Botstein et al., Miami Wntr. SyTnp. 19:265-274, 1982; Broach, In: "The Molecular Biology of the Yeast Saccharomyces: Life Cycle and Inheritance", Cold Spring Harbor Laboratory, Cold Spring Harbor, N.Y., p. 445-470, 1981; Broach, Cell 28:203-204, 1982; Dilon et at., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980.

Light generating protein encoding sequences can be cloned into any number of commercially available vectors to generate expression of the light generating polypeptide for use as a marker of transformation in an appropriate host system. These systems include, but are not limited to, the following: vectors for baculovirus transformation, Reilly, P. R., et al., *BACULOVIRUS EXPRESSION VECTORS: A LABORATORY MANUAL* (1992), Beames, et al., *Biotechniques* 11:378 (1991), Pharmingen; Clontech, Palo Alto, Calif.); vectors for bacterial transformation, Ausubel, F. M., et al., *CURRENT PROTOCOLS IN MOLECULAR BIOLOGY*, John Wiley and Sons, Inc., Media Pa., Clontech; vectors for yeast transformation, Rosenberg, S. and Tekamp-Olson, P., U.S. Pat. No. RE35,749, issued, Mar. 17, 1998, herein incorporated by reference, Shuster, J. R., U.S. Pat. No. 5,629,203, issued May 13, 1997, herein incorporated by reference, Gellissen, G., et al., *Antonie Van Leeuwenhoek,* 62(1-2):79-93 (1992), Romanos, M. A., et al., *Yeast* 8(6):423-488 (1992), Goeddel, D. V., *Methods in Enzymology* 185 (1990), Guthrie, C., and G. R. Fink, *Methods in Enzymology* 194 (1991); vectors for mammalian cell transformation, Clontech; Life Technologies/Gibco-BRL, Grand Island, N.Y., Haynes, J., et al., *Nuc. Acid. Res.* 11:687-706 (1983), Lau, Y. F., et al., *Mol. Cell. Biol.* 4:1469-1475 (1984), Kaufman, R. J., "Selection and coamplification of heterologous genes in mammalian cells," in *Methods in Enzymology, vol.* 185, pp 537-566. Academic Press, Inc., San Diego Calif. (1991); and vectors for use in plant cell transformation, plant cloning vectors, Clontech Laboratories, Inc., Palo Alto, Calif., and Pharmacia LKB Biotechnology, Inc., Pistcataway, N.J., Hood, E., et al., *J. Bacteriol.* 168:1291-1301 (1986), Nagel, R., et al., *FEMS Microbiol. Lett.* 67:325 (1990), An, et al., "Binary Vectors", and others in *Plant Molecular Biology Manual A*3:1-19 (1988), Miki, B. L. A., et al., pp. 249-265, and others in *Plant DNA Infectious Agents* (Hohn, T., et al., eds.) Springer-Verlag, Wien, Austria, (1987), *Plant Molecular Biology: Essential Techniques,* P. G. Jones and J. M. Sutton, New York, J. Wiley, 1997, Miglani, Gurbachan *Dictionary of Plant Genetics and Molecular Biology*, New York, Food Products Press, 1998, Henry, R. J., *Practical Applications of Plant Molecular Biology,* New York, Chapman & Hall, 1997.

Vectors comprising light generating protein coding sequences may also include sequences that facilitate single site recombination into the genome of a target organism (e.g., a single DNA sequence homologous to one or more site in the target genome used to facilitated integration) or sequences that facilitate homologous recombination (e.g., two sequences homologous to a locus in a target genome wherein the two sequences flank the light generating protein coding sequences (as well as any related control elements or further sequences of interest). Once identified, the targeting sequences can be readily isolated, for example by designing primers and amplifying the sequence by PCR. The amplified product can then be inserted into a light generating protein coding sequence-containing construct, for example flanking the sequences which are desired to be integrated. Integrating vectors may be circular or linear. Further, using the methods of the present invention vectors carrying light generating protein coding sequences (and related control elements as well as further sequences of interest) may be introduced into cells and random integration events detected by transformation of target cells and the identification of transformants.

Example 4 describes the construction of an integrative genomic targeting vector for *Candida albicans*, where the targeting vector comprises promoter containing light generating protein coding sequences. Further, Example 4 describes transformation experiments carried out using this vector. The results present in Example 4 demonstrate that light generating protein coding sequence-containing constructs can be used as reporter constructs in cells that are not amenable to selectable markers. The methods described in Example 4 employ a luciferase gene from the firefly *Photinus pyralis* altered to allow its expression in *C. albicans*. Transformed *Candida albicans* cells were isolated by screening for light production without use of any auxotrophic or drug-based selection.

The high density screening described herein involved no selection and provided an efficient method for obtaining transformants. Successful transformation occurred at a frequency of about $5 \times 10^{-5}$ to $10^{-6}$ (5-10 bioluminescent colonies/20 plates; Example 4). Identification of transformants (i.e., light producing cells) among the great excess of non transformed cells was straightforward and repeatable. The successful transformation demonstrated herein has been repeated with several virulent strains from ATCC. In one embodiment of the present invention, the transformation mix was plated on non-selective media containing luciferin. A lawn of cells were grown. The lawn was imaged for light production (using, for example, Xenogen Corporation IVIS™ imaging system (Xenogen Corporation, Alameda, Calif.)) to identify areas of cells containing and expressing the light producing protein coding sequences (e.g., luciferase gene). Four to eight small samples were picked from each bright region on the plate and used to inoculate overnight liquid cultures. Small aliquots of the overnight cultures were then mixed with luciferin in wells of a microtiter plate and each aliquot evaluated for light production. Overnight cultures comprising light generating protein coding sequence containing/expressing cells were diluted and plated for single colonies to obtain single colony isolates.

Accordingly, these results demonstrate that light generating protein coding sequence-containing constructs can be used for high-density screening to detect transformation events and, additionally, allow for observation in whole animals.

The vectors of the present invention, comprising light generating protein coding sequences, can be formulated into kits. Components of such kits can include, but are not limited to, containers, instructions, solutions, buffers, disposables, and hardware. Exemplary hardware may include an intensified photon-counting camera or a cooled integrating camera.

Thus, instead of using conventional selection or screening methods to determine the presence of a vector in a transformed cell, a light-based screening method may be employed. In one embodiment (i.e., a promoter containing construct), a light generating polypeptide coding sequence is placed under the control of a promoter active in an organism of interest. Such control elements may be constitutive or conditional. For example, the luxABCDE cassette, operably linked to a promoter sequence functional in the target organism of interest may be introduced into a suitable vector. The organism of interest is then transformed and the resulting organisms are screened for their ability to produce light. In this method, the production of light is used to identify transformants of interest. Light producing colonies (or patches of bacteria) are typically cloned (i.e., physically isolated) by standard methods (e.g., dilution plating, for example, using microtiter wells, or streaking for single colonies). One aspect of the present invention provides a vector comprising light-generating polypeptide sequences operably linked to promoter sequences functional in a target organism of interest. Using such a vector provides means for the transformation of organisms for which no selectable marker (such as a drug resistance marker) is available.

2C. Methods of Making Light Generating Protein Constructs

The light generating protein cassettes, transposon cassettes and shuttle vector constructs described herein can be assembled utilizing methodologies known in the art of molecular biology (see, for example, Ausubel, F. M., et al., *Current Protocols in Molecular Biology*, John Wiley and Sons, Inc., Media, Pa. (1995), or Sambrook, et al.) in view of the teachings of the present specification. Typically, gene cassettes comprising sequences encoding light-generating polypeptides are assembled. Promoters, control elements, and/or other nucleotide sequences can also be introduced into the constructs at suitable positions.

A preferred method of obtaining polynucleotides, suitable regulatory sequences and short, random nucleotide sequences is PCR. General procedures for PCR as taught in MacPherson et al., PCR: *A PRACTICAL APPROACH*, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination. Another method for obtaining polynucleotides, for example, is by enzymatic digestion. The components of a desired vector can be organized in any suitable orientations and/or configurations.

2D. Methods of Introducing Nucleic Acids Into Target Cells

Methods for the introduction of nucleic acids into cells (or protoplasts of cells, such as after the weakening or removal of yeast or plant cell walls) are known to those of skill in the art and include, but are not limited to, the following: lipid-mediated transfer (e.g., using liposomes, including neutral and cationic lipids), direct injection (e.g., microinjection), cell fusion, microprojectile bombardment (e.g., biolistic methods, such as DNA particle bombardment), co-precipitation (e.g., with calcium phosphate, or lithium acetate), DEAE-dextran- or polyethylene glycol-mediated transfer, and viral vector-mediated transfer.

The transformation method is typically chosen depending on the cell type and the amount of nucleic acid available for use in the method. After transformation the cells may be plated at a density that facilitates screening for light production. Cells can be plated at a number of densities, for example, by preparing a series of dilutions of the transformed cell population. Cell plating density differs by cell type; however, high-density plating for initial screening is generally preferred in order to increase the likelihood of detecting transformed cells in the population of cells treated by the transformation method.

One of ordinary skill in the art can apply the light-based screening methods of the present invention using essentially any selected transformation method combined with the guidance presented herein.

3. Evaluation of Light-Generating Polypeptide Sequences in Cell Culture

The light generating protein coding sequence constructs such as the ones described above and in the Examples, can be used to transform a variety of host cells and assay successful transformation events. Suitable host cells, include, but are not limited to, eucaryotes (e.g., yeast, such as *Candida* and *Saccharomyces*); plant cells; mammalian cells (e.g., BHK, VERO, HT1080, 293, RD, COS-7, or CHO cells); tissue-specific cells; tumor cells; insect cells; prokaryotes such as Gram-negative bacteria, Gram-positive bacteria and other genera not included in either of the preceding classifications (e.g., *Rickettsia* spp.; *Rochalimaea* spp,; *Coxiella* spp.; *Treponema* spp., including *Treponema pallidum*, the organism which causes syphilis; *Mycoplasma* spp., and *Chlamydia* spp.).

With respect to Gram-negative host cells, the constructs of the present invention may be used to transform organisms including but not limited to the following: *Clostridium* spp., *Vibrio* spp., *Brucella* spp., *Bordetella* spp., *Campylobacter* spp., *Pseudomonas* spp., *Escherichia* spp., *Enterobacter* spp., *Klebsiella* spp., *Serratia* spp., *Citrobacter* spp., *Proteus* spp., *Salmonella* spp., *Shigella* spp., and *Yersinia* spp.

With respect to Gram-positive host cells, the constructs of the present invention may be used to transform organisms including but not limited to the following:

Members of the Gram-positive cocci families Micrococcaceae (*Micrococcus* spp., *Stomatococcus* spp., *Planococcus* spp., and *Staphylococcus* spp.), Deinococcaceae (*Deinococcus* spp.), and species of other cocci genera including: *Streptococcus* spp (e.g., pyogenic hemolytic *streptococci* spp., oral *streptococci* spp., *Enterococci* spp., lactic acid *streptococci* spp., anaerobic *Streptococci* spp., and other species of *Streptococci*); *Leuconostoc* spp., *Pediococcus* spp., *Aerococcus* spp., *Gemella* spp., *Peptococcus* spp., *Peptostreptococcus* spp., *Ruminococcus* spp., *Coprococcus* spp., and species of the geneus *Sarcina*.

Endospore-forming Gram-positive rods and cocci including: *Bacillus* spp., *Sporolactobacillus* spp., *Clostridium* spp., *Desulfotomaculum* spp., *Sporosarcina* spp., and species of the genus *Oscillospira*.

Regular, nonsporing, Gram-positive rods, including *Lactobacillus* spp., *Listeria* spp. (including the pathogenic species *Listeria monocytogenes* found as contaminants in foodstuffs, in drinking water, and on food preparation surfaces), Genus *Erysipelothrix* spp., *Brochothrix* spp., *Renibacterium* spp., *Kurthia* spp., and species of the genus *Caryophanon*.

Irregular, nonsporing, Gram-positive rods, including *Corynebacterium* (including the plant pathogenic species of *Corynebacterium, Gardnerella* spp., *Arcanabacterium* spp., *Arthrobacter* spp., *Brevibacterium* spp., *Curtabacterium* spp., *Caseabacter* spp., *Microbacterium* spp., *Aureabacterium* spp., *Cellulomonas* spp., *Agromyces* spp., *Arachnia* spp., *Rothia* spp., *Propionibacterium* spp., *Eubacterium* spp., *Acetobacterium* spp., *Lachnospira* spp., *Butyrivibrio* spp., *Thermoanaerobacter* spp., *Actinomyces* spp., and species of the genus *Bifidobacterium*.

Organisms of the family Mycobacteriaceae, i.e., *Mycobacterium* spp.

The nocardioforms, including *Nocardia* spp., *Rhodococcus* spp., *Nocardioides* spp., *Pseudonocardia* spp., *Oerskovia* spp., *Saccharopolyspora* spp., *Micropolyspora* spp., *Promicromonospora* spp., and species of the genus *Intrasporangium*.

Organisms of special interest include: *Clostridium* spp., *Vibrio* spp., *Brucella* spp., *Bordetella* spp., *Campylobacter* spp., *Pseudomonas* spp., *Escherichia* spp., *Enterobacter* spp., *Klebsiella* spp., *Serratia* spp., *Citrobacter* spp., *Proteus* spp., *Salmonella* spp., *Shigella* spp., and *Yersinia* spp.

Transformation methods for both prokaryotic cells and eukaryotic cells are known in the art (e.g., Sambrook, et al.) and include, but are not limited to, calcium phosphate precipitation, microinjection or electroporation. Vectors containing the appropriate regulatory elements and multiple cloning sites are widely commercially available (e.g., Stratagene, La Jolla, Calif.; Clontech, Palo Alto, Calif.) and can be used as backbone vectors to carry the light generating protein coding sequences.

As described above, certain expression cassettes described herein require the addition of exogenous substrate for the production of light (e.g., luc and luxAB expression cassettes). In a one embodiment of the present invention, the substrate is aldehyde. When administered to cells, aldehyde may be applied in the atmosphere surrounding the culture media as a vapor or directly to the culture media as a liquid or solid.

Detection and quantification of light production is accomplished using, for example, an intensified photon-counting camera (Hamamatsu Photonics Model 2400-32). One system particularly useful for screening transformants generated by the methods of the present invention is the IVIS™ imaging system available from Xenogen Corporation (Alameda, Calif.). The IVIS™ imaging system includes a highly sensitive camera (e.g., a cooled integrating camera (Roper Scientific Model LN/CCD 1300-EB/I; Spectral Instruments model 620 cooled CCD camera, available from Spectral Instruments, Inc., Tucson, Ariz.), a specially designed imaging chamber, and software to run it all. In addition, the LivingImage™ software analyzes, organizes, and stores data. Typical specifications for the components of the system are as follows in Table 1.

TABLE 1

| Imaging Component | Specifications | Comments |
|---|---|---|
| Sensor | Back illuminated Grade 1 CCD | |
| Imaging Pixels | 1340 × 1300 | |
| Pixel Size | 20 um square | |
| Quantum Efficiency | ~85% | 450-700 nm |
| | >50% | 350-900 nm |
| Read Noise | <5 electrons RMS | |
| Dark Current | <100 electrons/s/cm$^2$ | |
| Min Detectable Luminescence | <100 photons/s/sr/cm$^2$ | 300s exposure, binning of 10, 10 cm field of view |
| Lens | f/.95-f/16 | |
| CCD Operating Temperature | −120° C. | |
| Field of View | 10-25 cm | |
| IVIS Darkbox Dimensions | 46 cm × 46 cm × 51 cm | L × W × H |
| Power Requirements | 15 A at 120 V | |

Multiple light generating protein coding sequences may be incorporated into a single organism using the constructs and methods described herein. In one embodiment, each cassette may encode a light generating polypeptide which emits light at a different characteristic wavelength relative to each other. Alternatively, several cassettes carrying light generating polypeptides which emit light at the characteristic wavelength may be used. Combinations of cassettes, comprising light generating protein coding sequences, having a variety of such mixtures of light generating polypeptides which emit light at a different characteristic wavelengths may be constructed in view of the teachings of the present specification.

4. Evaluation of Luciferase Expression Vectors in Animals

In addition to the constructs and methods of the present invention for use in transformation of a chosen cell or cell type, microorganisms carrying the constructs comprising light generating protein coding sequences are useful for non-invasive imaging in whole animals. Non-invasive imaging in whole animals is described in co-owned U.S. Pat. No. 5,650, 135, by Contag, et al., and herein incorporated by reference. (see, also, Contag, et al., (1998) *Nature Medicine* 4(2:245-247; Contag, et al., (1996) *OSA Tops on Biomedical Optical Spectroscopy and Diagnostics* 3:220-224; Contag, et al., (1997) *Photochemistry and Photobiology*, 66(4):523-531; and Contag, et al., (1995) *Mol. Microbiol.* 18:593-603.

In the imaging method, the conjugates contain a biocompatible entity (e.g., a transformed bacterium carrying a construct of the present invention integrated into its genome) and a light-generating moiety (e.g., a luciferase enzyme). Light-emitting conjugates are typically administered to a subject by any of a variety of methods, allowed to localize within the subject, and imaged. Since the imaging, or measuring photon emission from the subject, may last up to tens of minutes, the subject is typically, but not necessarily, immobilized during the imaging process.

Imaging of the light-emitting entities involves the use of a photo detector capable of detecting extremely low levels of light—typically single photon events—and integrating photon emission until an image can be constructed. Examples of such sensitive photo detectors include devices that intensify the single photon events before the events are detected by a camera, and cameras (cooled, for example, with liquid nitrogen) that are capable of detecting single photons over the background noise inherent in a detection system.

Once a photon emission image is generated, it is typically expressed as a pseudocolor image superimposed on a "photographic" reflected light image of the subject to provide a frame of reference for the source of the emitted photons (i.e. localize the light-emitting conjugates with respect to the subject). Such a "composite" image is then analyzed to determine the location and/or level of expression of a reporter gene in the subject.

4A. Infection of Animals

The cassettes described herein are useful in evaluating various procaryotic and eucaryotic cells in an animal. For example, the cassettes described can be integrated into the genome of pathogenic organisms (e.g., *Candida*, Gram-positive bacteria, etc.) and subsequently introduced into a whole animal. The animal can then be used to follow the infection process in vivo and to evaluate potential anti-infective drugs, such as new antibiotics, for their efficacy in inhibiting the infection. Thus, in one aspect, the expression cassettes described herein are useful in non-invasive imaging and/or detecting of light-emitting conjugates in mammalian subjects (e.g., infected with bacterial or fungal cells carrying a luciferase expression cassette). The transformed cells may be administered to a test subject such that they become localized in a cell or tissue type. Alternatively, the transformed cells can be administered such that they become uniformly distributed in the subject.

4B. Substrate Administration

As described above, certain expression cassettes described herein require the addition of exogenous substrate (e.g., luciferin) for the production of light (e.g., luc and luxAB expression cassettes). In one embodiment of the present invention, the substrate is aldehyde. The substrate may also be administered to the whole animals. Appropriate concentrations for the substrate can be empirically determined for each line of test animal constructed. The substrate (typically, luciferin) can be administered before, concomitantly with, or after the administration of the analyte of interest. The routes of administration of the substrate can be as described for the analyte. Preferred routes of administration for the substrate include, but are not limited to, intravenous or topical administration or by providing substrate in the atmosphere, for example, as a vapor.

5. Uses Of The Constructs Of The Present Invention

In one aspect, the present invention is directed to promoter containing or promoterless, light generating protein coding sequence constructs used as transformation vectors for a variety of cell types. The present invention allows the identification of cells into which the constructs of the present invention have been successfully introduced. This method described herein of using light production as a reporter of transformation is particularly useful for transformation of cell types where there are no known selectable markers that can be used, for example, antibiotic resistant bacteria, yeast with no auxotrophic markers. The transformation method of the present invention comprises the following steps. First a population of cells of the desired target cell is prepared, a light producing protein coding sequence construct is then used to transform the cells employing transformation methods known in the art, for example, (calcium precipitation; polyethylene glycol precipitation; lithium acetate/polyethyene glycol transformation, Braun and Johnson (1997) *Science* 277(5322): 105-9; and electroporation, De Backer, Maes et al. (1999) *Yeast* 15(15): 1609-18). Cell that have taken up the light producing protein coding sequence construct and which express the light producing protein are identified, for example, using an imaging system. Transformed cells are typically further purified to produce essentially pure cultures of transformed cells, by, for example, dilution plating or streaking for single colonies.

In one aspect of the present invention, a promoterless light generating protein coding sequence construct is used. In this case, expression of the light generating protein coding sequences is typically dependent on integration into the genome of the target cell, most commonly the integration event is adjacent active transcriptional control elements in the target cell.

In another aspect of the present invention, a promoter containing light generating protein coding sequence construct is employed. In this case the light generating protein coding sequences may be integrated in the genome of the target cell or carried on a plasmid (or other episomal or extrachromosomal vector).

The cassettes of the present invention is useful in a wide variety of applications. For example, they may be employed in conjunction with a gene or nucleic acid sequence of interest to assay whether the target cell has been transformed with the gene or nucleic acid sequence of interest. In other words, light serves as a reporter which indicates successful transformation of the target cell (e.g, pathogenic organisms) via, for example, electroporation, or phage-mediated transduction or conjugation. This is especially useful in cells that cannot make use of selectable markers (such as drug resistance) that are typically used to assay for transformation events.

Transformants may also be used to identify effective pharmaceutical agents and determine their point of action. After isolating a successfully transformed target cells, the target cell can then be used to infect multiple groups of experimental animals, each group containing one or more of the genes or nucleic acid sequences of interest and/or active promoters. The group is then treated with the pharmaceutical agent of interest, and both the experimental animals and infected, untreated control animals are then monitored for light production. Agents effective in suppressing transcription and/or translation (either directly or indirectly) or that perturb the ability of the transformed cell to function normally will suppress light production in the treated experimental animals, while light production will be observed in the corresponding infected, untreated control animals. Alternatively, compounds enhancing light production may also be identified.

Organisms modified to produce light as taught by the present invention can be used to monitor the presence of microorganisms, for example, in infections, foodstuffs, in drinking water, and on food preparation surfaces.

In particular, the methods of the present invention are useful for introducing nucleic acids (e.g., DNA) into cells wherein it is difficult to select transformants, for example, pathogenic eucaryotic organisms (e.g., *Candida*), and antibiotic-resistant bacteria, including, but not limited to, nosocomial pathogens (e.g., methicillin-resistant strains of *Staphylococcus aureus, Enterococcus faecium*, and other antibiotic resistant enterococci).

Below are examples of specific embodiments for carrying out the present invention. The examples are offered for illustrative purposes only, and are not intended to limit the scope of the present invention in any way.

MATERIALS AND METHODS

Unless indicated otherwise, manipulation of cells, proteins and nucleic acids (e.g., DNA) were performed using standard methods, as described in, e.g., Sambrook, et al., and Ausubel, F. M., et al., *Current Protocols in Molecular Biology*, John Wiley and Sons, Inc., Media, Pa. (1995). Unless indicated otherwise, restriction enzymes were obtained from New England Biolabs, modifying enzymes were obtained from Promega or Boehringer Mannheim, and other laboratory chemicals were obtained from Sigma Chemical Company (St. Louis, Mo.).

Efforts have been made to ensure accuracy with respect to numbers used (e.g., amounts, temperatures, etc.), but some experimental error and deviation should, of course, be allowed for.

A. In Vitro Screening in Presence of Exogenous Aldehyde

Exogenous aldehyde substrate was added prior to imaging plates or cultures of bacteria not containing the luxCDE genes. For imaging plates, n-decyl aldehyde (decanal; Sigma Chemical Company) was spread on the inside surface of lids covering the plates containing the bacteria to be imaged ("aldehyde vapor imaging"), and the plates then imaged using an intensified CCD camera (Hamamatsu Photonics model 2400-32) essentially as described in U.S. Pat. No. 5,650,135. For imaging liquid cultures, 1 μl of a 1% decanal solution (in 50% ethanol) was added to 1 ml of the appropriate 10-fold dilutions of the culture.

B. Preparation of DNA and Cloning

Unless indicated otherwise, following digestion with one or more restriction endonucleases, DNA samples were heated to 85° C. for 15 min to inactivate the restriction enzymes. Ligations were performed at 16° C. overnight.

C. Transformation of Bacterial Cells

Preparation of Competent Cells. Unless indicated otherwise, bacterial cells were transformed as follows. Bacterial cultures were grown overnight in LB. Five ml of each culture were used to inoculate fresh 500 ml volumes of LB. These cultures were shaken at 37° C. until an O.D (600 nm) of approximately 0.6 was reached. The cells were then chilled on ice for 30 min before being harvested by centrifugation at 3,000× g for 10 min at 4° C. The cells were resuspended in 50 ml of either cold 0.5 M sucrose (*S. aureus*) or ddH$_2$O (*E. coli*), before being re-centrifuged and resuspended in 5 ml of either cold 0.5 M sucrose (*S. aureus*) or ddH$_2$O (*E. coli*). At this stage, the cells were held on ice for 30 min, and then re-centrifuged and resuspended in 5 ml of cold 10% glycerol. Aliquots of each cell type were frozen down and stored at −80° C.

Electroporation. Plasmid DNA was purified using a Qiagen column, dialyzed, and electroporated into competent cells using a "GenePulser" (BioRad). The settings were 25 μF, 2.5 kV, and either 100 ohms resistance for *S. aureus*, or 400 ohm resistance for *E. coli* and *S. pneumoniae*. The cells were left to recover in 1 ml of culture medium 2 hr at 37° C. before being plated on a suitable agar containing the requisite selection antibiotic.

D. Imaging Samples

Samples were imaged essentially as described in Contag, et al., U.S. Pat. No. 5,650,135, with minor modifications as indicated below.

In experiments performed in support of the present invention (detailed below), the amount of light generated by a sample was quantified using either an intensified photon-counting camera (Hamamatsu Photonics Model 2400-32) or a cooled integrating camera. With respect to the cooled integrating type of camera, the particular instrument used was chosen from among three makes/models: (1) Princeton Instruments Model LN/CCD 1340-1300-EB/1; (2) Roper model LN-1300EB cooled CCD camera (available from Roper Scientific, Inc., Tucson, Ariz.); and (3) Spectral Instruments model 600 or model 620 cooled CCD camera (available from Spectral Instruments, Inc., Tucson, Ariz.). The preferred apparatus was the Hamamatsu Photonics camera number XEN-3 and the Princeton Instruments camera number XEN-5, respectively, both located at Xenogen Corporation, Alameda, Calif. Both types of cameras use a charge-coupled device array (CCD array), to generate a signal proportional to the number of photons per chosen unit area. The chosen unit area may be as small as that detected by a single CCD pixel, or, if binning is used, that detected by any selected group of pixels. This signal may optionally be routed through an image processor, such as the Argus available from Hamamatsu Photonics, and is then transmitted to a computer (either a PC running Windows NT (Dell Computer Corporation; Microsoft Corporation, Redmond, Wash.) or a Macintosh (Apple Computer, Cupertino, Calif.) running an image-processing software application, such as "LivingImage" (Xenogen Corporation, Alameda, Calif.). The software and/or image processor are used to acquire an image, stored as a computer data file. The data generally take the form of (x, y, z) values, where x and y represent the spatial coordinates of the point or area from which the signal was collected, and z represents the amount of signal at that point or area, expressed as "Relative Light Units (RLUs).

To facilitate interpretation, the data are typically displayed as a "pseudocolor" image, where a color spectrum is used to denote the z value (amount of signal) at a particular point. Further, the pseudocolor signal image is typically superimposed over a reflected light or "photographic" image to provide a frame of reference.

It will be appreciated that if the signal is acquired on a camera that has been calibrated using a stable photo-emission standard (available from, e.g., Xenogen Corporation), the RLU signal values from any camera can be compared to the RLUs from any other camera that has been calibrated using the same photo-emission standard. Further, after calibrating the photo-emission standard for an absolute photon flux (photons emitted from a unit area in a unit of time), one of skill in the art can convert the RLU values from any such camera to photon flux values, which then allows for the estimation of the number of photons emitted by a transformed cell in the sample per unit time.

E. Quantification of Light Output Using 96-Well Microtiter Plates

The amount of light generated by cells in solution was quantified by plating dilutions of the solution into wells of a 96-well plate, and imaging the plate as described above in the Xen-3 camera. The LivingImage software was then used to superimpose defined borders around the each area of the image showing a signal corresponding to light from a particular well. The signal from each of these areas was then quantified, and expressed as a single RLU value for each well. These RLUs were used in several of the studies detailed below, including Examples 13, 14 and 15.

EXAMPLE 1

Construction of a Gram-Positive lux Transposon: Tn4001 luxABCDE km$^R$

The luxABCDE km$^R$ cassette was constructed as follows: A Gram-positive kanamycin cassette from pDL289 (Buckley, N. D., et al. (1995) *J. Bacteriol.* 177:5028-5034) was PCR amplified using the primers KanF2 (5'-CTG TAG ACT CGA GGA GGG AAA TAA TAA ATG GC; SEQ ID NO: 1; the bolded letters represent a XhoI site) and KanR2 (5'-CAG AGT GTC GAC AGT TGC GGA TGT AC; SEQ ID NO:2; the bolded letters represent a SalI site). Amplification was carried out for 30 heating/cooling cycles of 15 seconds at 95° C., 30 seconds at 50° C., and 2 minutes at 72° C.

The resulting amplification product provided a promoterless km$^R$ antibiotic resistance gene. The amplification product was then cut with XhoI/SalI and ligated into the SalI site of the pSK-luxABCDE plasmid construct (see, co-pending and co-owned application U.S. Ser. No. 09/657,289 for further details about plasmid construction) directly downstream of the luxABCDE cassette.

The pSK luxABCDE km$^R$ plasmid construct was electroporated into *E. coli* DH5α cells and the transformed bacteria were plated onto LB plates containing 25 µg/ml kanamycin. After incubation at 37° C. overnight, the resulting transformants were screened for light production (see Materials and Methods) using a photon-counting CCD camera (Hamamatsu Photonics, Shizuoka Pref., Japan; model 2400-32). Expression of both kanamycin resistance and bioluminescence in *E. coli* (Gram-negative) were mediated by the lacZ promoter found in the pBluescript II SK+ or SK− vector backbone. DNA was prepared from bioluminescent colonies. The correct orientation of the kanamycin cassette (i.e., the coding sequence) relative to the luxABCDE coding sequences was confirmed by restriction digestion of the DNA with SalI and analysis of the resulting restriction patterns.

To construct a Tn4001 cassette containing the lux and km$^R$ genes, the luxABCDE km$^R$ cassette was cut from the pSK luxABCDE km$^R$ construct, prepared above, using SpeI/SalI. The ends of the fragments were filled in with nucleotides to generate blunt-ended molecules. These molecules were ligated into the EcoRV site of the plasmid pMGC57 (Lyon et al. (1998) *EMBO J.* 17:6263-6275) and the constructs electroporated into DH5α cells. The transformed bacteria were plated onto LB media containing 15 µg/ml chloramphenicol. The resulting transformants were screened for light production, chloramphenicol-resistance (CmR) and kanamycin-resistance (KanR). DNA was prepared from light-generating, CmR, KanR colonies. The correct orientation of the luxABCDE km$^R$ cassette, i.e., the location of the 5' end of the luxA sequence relative to the 5' end of the Tn4001 transposon, was confirmed by restriction digestion (XhoI/NdeI and XhoI/EcoRV) and restriction pattern analysis, as well as, by PCR analysis of DNA. PCR was carried out using the primers MGC-CAT-F1 (5'-GGT GTC CCT GTT GAT ACC G-3', SEQ ID NO:3) and LuxA-Rev (5'-CCA CAC TCC TCA GAG ATG CG-3', SEQ ID NO:4) under conditions detailed supra. The correct orientation was identified by fragment size.

EXAMPLE 2

Construction of Tn4001 luxABCDE km$^R$ Shuttle Vector Constructs

A. Construction of the pAUL-A Tn4001 luxABCDE km$^R$ Shuttle Vector

The Tn4001 cassette containing the lux and km$^R$ genes (designated IR luxABCDE km$^R$ tnp IR, where, IR represents inverted repeats and tnp represents the gene encoding the Tn4001 transposase) was inserted into a broad-range shuttle vector having a gram negative origin of replication and a gram positive origin of replication (either constitutive or conditional, e.g., temperature sensitive). One example of such a shuttle vector is the pAUL-A vector (Chakraborty, et al. (1992) *J. Bacteriol.* 174:568-574) which contains an erythromycin resistance gene that is functional in both Gram-positive and Gram-negative bacteria. This vector contains both a Gram-negative origin of replication and the temperature-sensitive pE194 Gram-positive origin of replication.

Herein the transposon cassettes of the present invention are schematically represented as follows. The inverted repeats (IR) generally indicate the ends of the transposable element. Accordingly one designation for the transposon is IR-tnp-IR, where tnp designates the gene encoding the transposase. Further elements can be added to the transposon and are indicated similarly, e.g., addition of a luxABCDE km$^R$ cassette is rendered schematically as IR luxABCDE km$^R$ tnp IR.

The IR luxABCDE km$^R$ tnp IR cassette was cut from pMGC57 using the enzymes EcoRI/XhoI and ligated into the EcoRI/SalI sites of the pAUL-A shuttle vector to give the shuttle vector construct pAUL-A Tn4001luxABCDE km$^R$.

*E. coli* cells (DHα5) were transformed with the shuttle vector construct by electroporation, plated onto LB plates containing erythromycin at a concentration of 150 µg/ml, and incubated at 37° C. overnight. The resulting transformants were screened for light production, erythromycin-resistance (EmR) and kanamycin-resistance (KanR). Plasmid DNA was then isolated from light-generating, ErR, KanR colonies.

B. Construction of the pSK Tn4001 luxABCDE km$^R$ pE194 Shuttle Vector

As an alternative to using pAUL-A as a delivery system for the Tn4001 luxABCDE construct, the plasmids pSK and pE194 were used in combination.

The Tn4001 cassette was moved from pMGC57 into pSK as follows: The Tn4001 cassette was cut from pMGC57 using XhoI/PstI and ligated with similarly cut pSK. This ligation was electroporated into competent *E. coli* DH5α and transformants selected on LB containing 100 µg/ml ampicillin, IPTG, X-gal. White colonies were screened by PCR using the primers including sequences from the Tn4001 transposase gene. Colonies indicated to be positive by PCR were plasmid prepped and these DNA's cut with XhoI/PstI to confirm that they contained the correct size fragment.

The luxABCDE km$^R$ cassette was then moved into pSK Tn40001 so that it lay between the two IR sequences. First, the ampicillin cassette was removed from pSK luxABCDE km$^R$ using the enzymes AhdI/KpnI (in order to aid subsequent cloning of the lux cassette into pSK Tn40). The luxABCDE km$^R$ cassette was then excised from the ampicillin deleted pSK backbone with BamHI/XhoI. The pSK Tn4001 DNA was then cut with EcoRV and ligated with the blunt-ended luxABCDE km$^R$ cassette.

The ligation was electroporated into competent *E. coli* DH5α and transformants selected on LB containing 100 µg/ml ampicillin. Light transformants were patched on either chloramphenicol or kanamycin. The correct orientation of the positive clones was confirmed by PCR using the primers M13F and LuxA-R.

Next, pSK Tn4001 luxABCDE km$^R$ was linearized with SacI and blunt-ended. Finally, this DNA was then ligated with blunt-ended ClaI-cut pE194, resulting in the pSK Tn4001 luxABCDE km$^R$ pE194 shuttle vector construct.

This construct was electroporated into competent E. coli DH5α. Transformants were selected on LB containing 150 µg/ml erythromycin. Resulting light colonies were then patched onto LB containing 100 µg/ml ampicillin and LB containing either 50 µg/ml kanamycin or 15 µg/ml chloramphenicol.

C. Construction of the pE194 Tn4001 pSK luxABCDE km$^R$ Shuttle Vector

A Tn4001 luxABCDE km$^R$ shuttle vector was constructed wherein the Gram-negative origin was located inside of the two IR sequences. Firstly, the Gram-negative Tn4001 containing plasmid pMGC57 was fused with the Gram-positive erythromycin resistance plasmid pE194. pMGC57 was cut with PstI/BamHI and blunt-ended. At the same time pE194 was cut with ClaI and blunt-ended. These two linearized plasmids were then ligated and this mix was electroporated into competent E. coli DH5α and transformants selected on LB containing 150 µg/ml erythromycin.

Secondly, the chloramphenicol resistance cassette and the Gram-negative origin were removed from the pMGC57/pE194 composite. Plasmid DNA purified from a number of above erythromycin resistant colonies was cut with KpnI/XhoI (sites flanking the chloramphenicol resistance cassette and the Gram-negative origin) and a proportion of each digest was run on an agarose gel to identify a plasmid of the correct size. The remainder of a plasmid digest appearing to be the correct size was then blunt-ended and ligated. This ligation was electroporated into S. aureus RN4220 and plated onto chocolate agar containing 0.3 µg/ml erythromycin.

Finally, the pSK luxABCDE km plasmid was introduced within the IR of Tn4001. Plasmid DNA purified from 10 of the pMGC57/pE194 ori cm$^R$ S. aureus clones was cut with EcoRV and a proportion of each digest was run on an agarose gel to identify a plasmid of the correct size. The remainder of a plasmid digest showing the correct size (approximately 6 kb) was then ligated with blunt-ended BamHI cut pSK luxABCDE km DNA. This ligation was electroporated into DH5a and transformants selected on LB containing 150 µg/ml erythromycin. Bioluminescent colonies were then patched in duplicate onto LB plates containing either 50 µg/ml kanamycin or 100 µg/ml ampicillin to confirm the activity of the latter antibiotic cassettes. Since the probability of pSK luxABCDE km ligating into the former plasmid in the correct orientation should be approximately 50%, it was decided that such variants could be identified by phenotype in S. aureus (only plasmids with lux in the correct orientation imparting bioluminescent upon transposition).

EXAMPLE 3

High-Density Screening of Bioluminescent Transposants

As an alternative to the use of selective media, bioluminescent colonies were isolated from among colonies plated at high density on solid medium using optical detection and manual isolation.

S. aureus 8325-4 cells were transformed with pE194 Tn4001 luxABCDE, plated on solid non-selective media plates at a density of $10^4$ to $10^5$ cells per plate, and grown overnight at 37° C. Strongly bioluminescent single colonies were detected using an ICCD camera, and those colonies were picked using a disposable micropipette tip; the light producing phenotype of the desired colony was confirmed using the camera. The colony was used to inoculate a volume of liquid growth medium, which was then streaked onto fresh media plates. The plates were incubated overnight at 37° C. The process was repeated until isolation of a pure colony was confirmed by observation of essentially uniform light intensity among single colonies on the streaked plates.

The preceding demonstrates a method that avoids the need for an antibiotic selection as a means of isolating organisms of interest transformed with the transposon cassettes of the present invention.

EXAMPLE 4

Construction of an Integrative Genomic Targeting Vector for *Candida albicans*, Transformation and Screening of *C. albicans* and Uses of Transformed Strains A. Vector Construction In order to express luciferase in *Candida albicans*, CTG codons in the open reading frame (ORF) of the luciferase gene were altered as follows. First, the luciferase gene in pGL2-Basic was cut into two pieces to facilitate the mutagenesis of all nine CTG codons to TTG codons. One fragment contained four CTG codons and the other five CTG codons. These were cloned separately into pBluescript II KS(+). The codons were altered using the QuikChange™ site-directed mutagenesis kit (Stratagene). After each mutagenesis step, products were sequenced to confirm that the desired mutations were incorporated.

Briefly, plasmid pGL2-Basic (Promega) containing a *Photinus pyralis* luciferase gene was restricted with XbaI and EcoRI and a 540 bp fragment containing four of the CTG codons in the luciferase open reading frame was cloned into pBluescript II KS(+) (Stratagene). A second, 751 bp EcoR I-EcoR V fragment containing the other five CTG codons was cloned separately into pBluescript II KS(+). These nine CTG codons were mutated by the QuikChange™ site-directed mutagenesis kit (Stratagene) to TTG. Pairs of complimentary primers were constructed for use with the site-directed mutagenesis kit. FIG. 1 presents the complimentary oligonucleotide pairs used for site directed mutagenesis of luciferase. These oligonucleotides were used to incorporate silent mutations by site-directed mutagenesis into the *Photinus pyralis* luciferase gene of pGL2 Basic. Nucleotides highlighted in bold are changes needed to change CTG to TTG. Underlined nucleotides are base changes needed for primer stability. These changes do not affect the amino acid sequence of the protein. Further, for primers RR45T and RR45B, two of the CTG to TTG mutations were in close enough proximity that both were incorporated in one reaction.

After mutagenesis of all 9 codons, the Xba I-EcoR I and EcoR I-EcoR V fragments containing the mutations were excised from pBluescript II KS(+) and cloned back into pGL2-Basic to produce pLucT9.

In addition to modifying luciferase codons, the constructs were also made to include a promoter and polyadenylation signal, both derived from *Candida*. To this end, pBluescript II KS+ was cut with Not I, the ends filled in, and a phosphorylated Asc I linker (5'-AGGCGCGCCT-3'; SEQ ID NO:21) was ligated into the blunt site to produce pBS-ASC. The luciferase open reading frame containing the nine TTG codons was amplified by PCR from pLucT9 with the primers LUCB and LUCP (FIG. 2A), producing a product that contains the modified luciferase open reading frame directly flanked by Bam HI and Pst I sites. The amplified product was restricted with Bam HI and Pst I and cloned into pBS-ASC to produce the plasmid pBS-L. The transcriptional termination region of the *C. albicans* actin (ACT1) gene (Delbruck and Ernst (1993) *Mol Microbiol* 10(4):859-66) was amplified by PCR from CAI4 genomic DNA with the primers ACT-TP and ACT-TH (FIG. 2A), cut with Pst I and Hind III, and ligated into pBS-L to produce pBS-LA.

The promoter of the *C. albicans* Enolase gene (ENO1) (Sundstrom and Aliaga (1992) *J Bacteriol* 174(21):6789-99) was amplified by PCR from *C. albicans* strain CAI4 DNA with the primers ENOA and ENOB (FIG. 2A). The ENO1 promoter was chosen because it was shown to have unregulated constitutive expression (Postlethwait and Sundstrom (1995) *J Bacteriol* 177(7):1772-9).

The amplified PCR product was cut with Asc I and Bam HI and cloned into pBS-LA cut with the same restriction enzymes to produce pBS-ELA. Thus, the ENO1 promoter was fused to the altered luciferase open reading frame via a Bam HI site inserted immediately upstream of the luciferase start codon. A Pst I site was placed immediately after the stop codon of the luciferase gene.

The multiple cloning site of pBluescriptII KS(+) from the Not I site to the Xho I site was replaced with a synthetic linker containing the restriction enzyme sites Not I, Asc I, Hind III, Fse I, SbfI, and Xho I (FIG. 2A; synthetic linker A, SEQ ID NO:34; synthetic linker B, SEQ ID NO:35; and FIG. 2C shows the complementary pairing of these two synthetic linkers) to produce pBS-NX. The promoter-luciferase-terminator cassette was excised from pBS-ELA with Asc I and Hind III and cloned into pBS-NX to produce pNX-ELA. The URA3 gene was amplified from the *C. albicans-E. coli* shuttle plasmid pRC2312 (Cannon (1992), supra) by PCR with the primers URAH and URAF (FIG. 2A). The amplified product was cut with Hind III and Fse I and ligated into pNX-ELA to produce pNX-ELAU.

For pilot experiments in the ura3::imm434/ura3::imm434 CAI4 strain, the targeting vector contained a complete *C. albicans* URA3 gene, which restored uracil prototrophy to the cells. In high density screening (see below), selection for URA3 function was not carried out with the clinical isolates ATCC 32032, 10261, and 90234.

All plasmid isolations and enzymatic reactions were carried out under standard conditions (Ausubel, supra; Sambrook, supra) or according to the manufacturer's instructions. All ligations were electroporated into the *Escherichia coli* strain DH5α (Life Technologies, Rockville Md.), and grown in Luria-Bertani (LB) medium containing 100 μg of ampicillin per ml. PCR was performed with a Geneamp PCR System 9700 automated thermal cycler (Applied Biosystems). Reactions were carried out in thin walled 200 μl PCR tubes in a volume of 50 μl containing 25 pmole of each oligonucleotide primer (Operon), 5 μl of 10× PCR buffer (supplied with Taq DNA polymerase; Life Technologies), 2 mM $MgCl_2$, 0.2 mM of each deoxynucleosidetriphosphate (dCTP, dGTP, dTTP, and dATP; Amersham), 1 U of Taq DNA polymerase (Life Technologies) and 1 ng of template DNA. Amplification was carried out under the following conditions: 40 cycles at 94° C. for 30 seconds, 50° C. for 30 seconds, 72° C. for 1-2 minutes (depending on the expected size of the product) and a final extension step of 72° C. for 5 minutes. Before restriction of PCR products, the reaction mixture was passed through spin columns (PCR purification kit; Qiagen).

*C. albicans* targeting sequences were also chosen and inserted into the vector. At the time of construction of the targeting vector, the sequence of six cosmids containing *C. albicans* genomic DNA were downloaded from GenBank (accession numbers: AL033501, AL033497, AL033503, AL033502, AL033396, and AL033391). Putative open reading frames from sequence data annotations were mapped using DNA Construction Kit 2™ (Textco, West Lebanon, N.H.). Several regions of approximately 3 kb that did not contain any putative open reading frames were examined for repeated Candida sequences (Chibana, Magee, et al., (1998) *Genetics* 149(4):1739-52) or homology to other possible open reading frames (ORFs). Large regions (~3 kb) not containing any putative open reading frames were divided into 500 by sections and each one was used in a blast search (Altschul, S. F., et al., (1990) *J Mol Biol* 215(3):403-10; Altschul, S. F., et al., (1997) *Nucleic Acid Res.* 25(17):3389-3402) of all known *Candida* sequences at that time (Stanford DNA Sequencing and Technology Center website)

Regions that had significant homology to known genes or repeated sequences were removed from consideration. A region in cosmid CA41C10 (GenBank accession number AL033501) from nucleotides 2356 to 5858 was selected. In this 3502 bp region the first and last 1000 bp were removed from consideration so as to not to include any promoters that may be present from adjacent open reading frames. The fragments that were selected for the 5' and 3' targeting regions of the vector are separated by 125 bp in the *Candida* genome. The genomic targeting region of the strains used was sequenced from PCR products amplified from genomic DNA. The regions in the published cosmid sequence and ATCC 32032 were identical except that ATCC3202 had an adenine residue instead of a guanine residue at nucleotide 4745. The other three strains had a guanine at nucleotide 3942, a thymidine at nucleotide 4645 and a tandem duplication of the nucleotides 4007-4131.

Selected targeting regions were cloned into the targeting vector flanking the luciferase expression cassette and the URA3 gene. In particular, nucleotides 3852 to 4307 of CA41C10 was amplified by PCR from CAI4 DNA by primers TAR5N and TAR5A (FIG. 2B). The amplified product was cut with Not I and Asc I and cloned into pNX-ELAU to produce pNX-5ELAU. Another region, from nucleotides 4436 to 4789 was amplified by PCR from CAI4 DNA by primers TAR3F and TAR3S (FIG. 2B). The amplified product was cut with Fse I and SbfI and cloned into pNX-5ELAU to produce pGTV-Eno. Kpn I sites are located near the outer ends of each these targeting regions. The construct was cut with Kpn I before using it for transformation of *Candida albicans*.

Figure 3B:
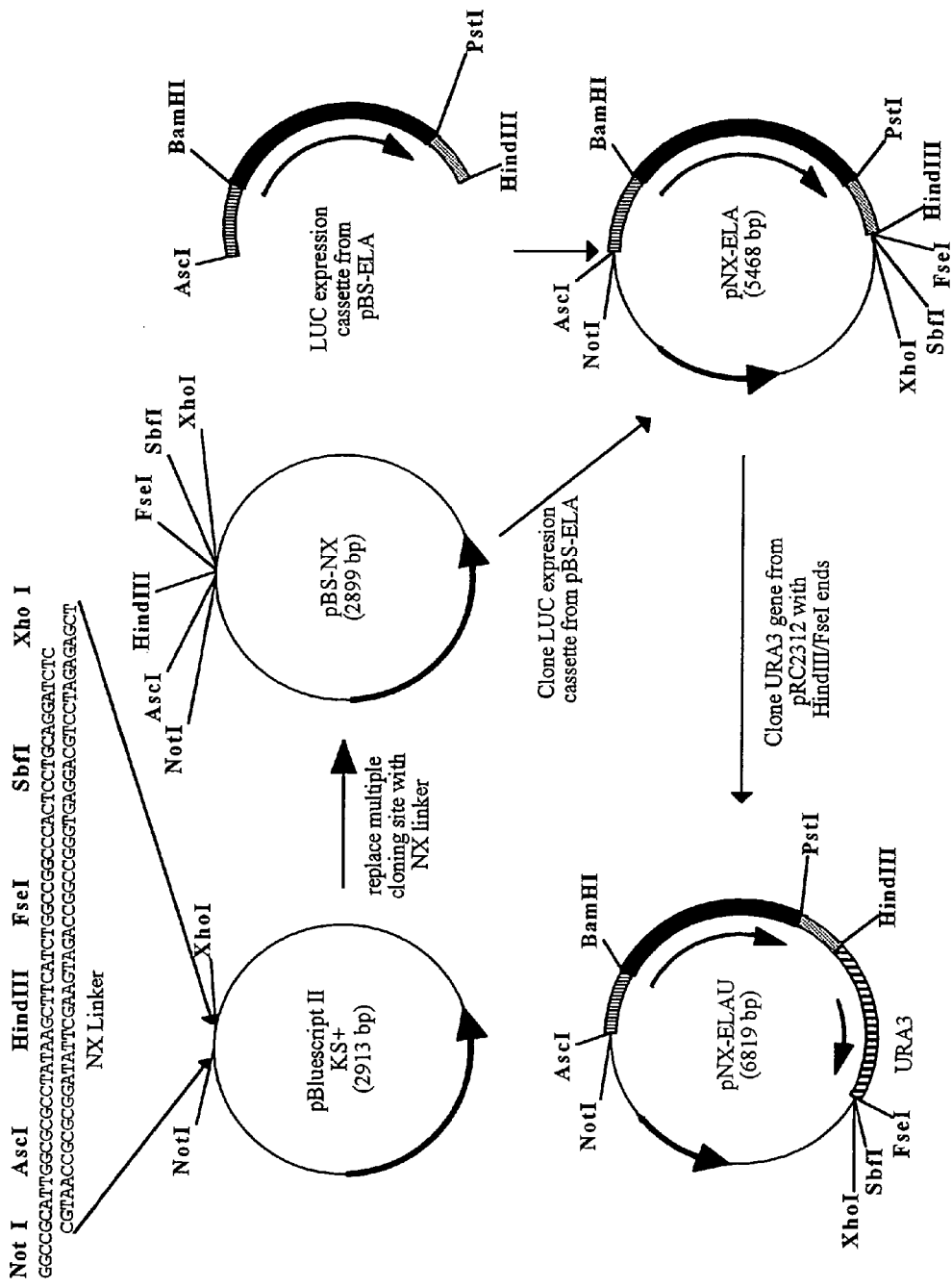
Figure 3C:
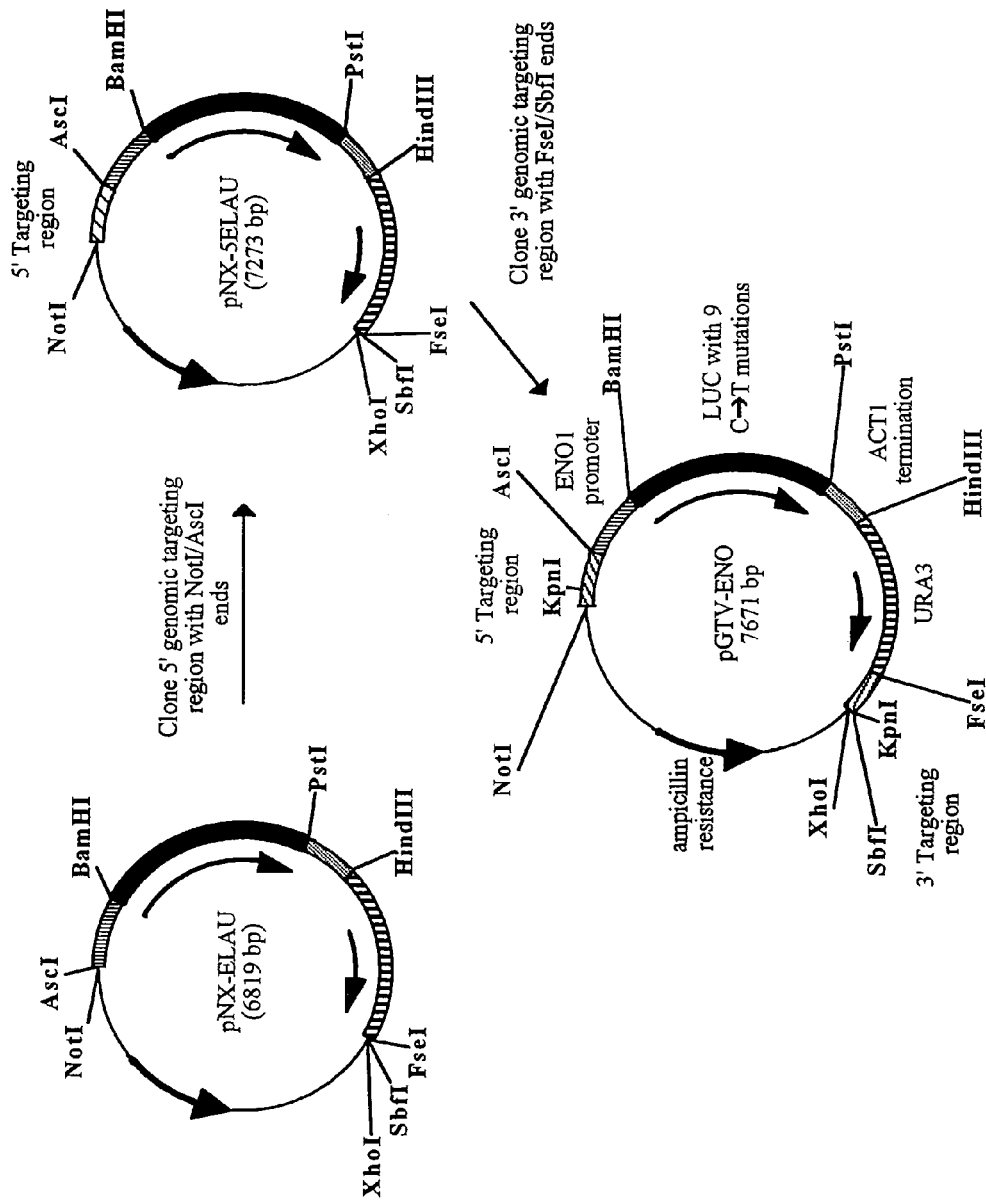

The construction of pGTV-ENO is graphically represented in FIGS. 3A, 3B, and 3C.

B. Transformation of *Candida albicans* Strains

The targeting construct was then used to transform *Candida albicans* using a modification of the method of Braun and Johnson (Braun and Johnson (1997) *Science* 277(5322): 105-9) was used for all *Candida albicans* transformations. 100 ml cultures were grown in YPD supplemented with 50 mg/ml uridine (Sigma), overnight at 30° C. The overnight cell cultures were diluted in the same media and allowed to grow to an $OD_{600}$ of 1-1.5. Cells were pelleted at 4000 rpm for 5 minutes and resuspended in 20 ml LATE buffer (100 mM Lithium acetate, 10 mM Tris HCl (pH 7.5), 1 mM EDTA). Cells were pelleted again, and resuspended in 1 ml of LATE buffer. 100 μl of cells were mixed with 10 μl of 10 mg/ml denatured, sheared salmon sperm DNA (Sigma) and 1-10 μg of Kpn I digested plasmid DNA. 700 μl of PLATE (40% polyethylene glycol 3350 in LATE buffer) was added and mixed gently with a micropipettor. Transformation reactions were incubated at 30° C. for 3 h and heat shocked at 42° C. for 45 minutes. Cells were pelleted and resuspended in 400 μl of YPD and plated on non-selective media containing luciferin.

*C. albicans* CAI4 (ura3::imm434/ura3::imm434) (Fonzi and Irwin (1993) *Genetics* 134(3):717-28) was kindly provided by Dr. Judith Berman, University of Minnesota, USA. *C. albicans* strains ATCC 32032, 10261, and 90234 were obtained from the American Type Culture Collection (Manassas, Va.). YPD medium (Qbiogene, Carlsbad, Calif.) contains 2%(w/v) peptone, 1%(w/v) yeast extract, and 2% (w/v) glucose. Synthetic defined (SD)(Qbiogene) media contains 0.17% (w/v) yeast nitrogen base without amino acids, 0.5% (w/v) ammonium sulfate, 2% (w/v) dextrose (glucose), and 0.077% (w/v) Complete Supplement Mixture without uracil (CSM-ura). The formulation for CSM-ura is as follows with components given in mg/L: Adenine 10; L-Argenine 50; L-Aspartic acid 80; L-Histidine-HCl 20; L-Isolucine 50; L-Leucine 100; L-Lysine 50; L-Methionine 20; L-Phenylalanine 50; L-Threonine 100; L-Tryptophan 50; L-Tyrosine 50; and Valine 140; TOTAL 770 mg. 770 mg (0.77 g) of this powder is added to IL of SD to make SD-ura. For growth on plates agar (Difco, Becton Dickinson, Franklin Lakes, N.J.) was added to 1.5% (w/v).

C. High Density Screening

For high density screening, transformed cells were transformed with a linearized pGTV-Eno construct and the transformed cells resuspended in 1 ml YPD, plated on twenty 140 mm SD-ura plates supplemented with 50 µg/ml uridine, containing 600 µg/ml luciferin (Biosynth, Naperville, Ill.) (at a density of approximately $2.5 \times 10^5$ cells/plate), and grown overnight at 30° C. Plating on this media provided better light production (relative to plating cells on YPD media). The media used allowed growth of untransformed and transformed cells alike, thus affording no selective pressure. Consequently, a lawn of cells grows on each plate.

The next morning the plates were imaged on the IVIS™ imaging system for 5 minutes using the IVIS™ imaging system (Xenogen Corporation). LivingImage™ software (Xenogen Corporation, Alameda, Calif.) was used to acquire and analyze the images. In certain cases, liquid cultures and plates were imaged using a photon counting intensified charged couple device (ICCD) camera (model 2400-32, Hamamatsu Photonics, Bridgewater, N.J.).

The low number of transformed cells that are bioluminescent can be detected against the dark background of many untransformed cells. At the high density of plating, it is difficult to pick a pure colony of bioluminescent cells. Therefore, cells were picked from the plate at and around the location of the bioluminescent colony, transferred to 1.5 ml microcentrifuge tubes and grown overnight at 30° C. in SD-ura supplemented with 50 µg/ml uridine. An aliquot from each tube was placed in the wells of a 96 well microtiter plate with SD-ura containing 600 µg/ml of luciferin. Plates were imaged for five minutes and cultures containing bioluminescent cells were diluted and spread on SD-ura plates supplemented with 50 µg/ml uridine for single colony isolation. The resulting bioluminescent cells were passaged repeatedly and were stable with no loss of signal. In addition, the growth rate of Candida containing the construct integrated at the targeting region is the same as the parental cells.

D. Southern Blotting

Genomic DNA from transformants of the clinical yeast strains ATCC 32032, 10261, and 90234 was isolated according to Fujimura and Sakuma (Fujimura and Sakuma (1993) Biotechniques 14(4):538-40). The genomic DNA was Southern blotted and probed with a fragment spanning the genomic targeting regions. In all three transformed strains the construct was integrated at the correct location in the genome.

E. Vaginal Infections

Female BALB/c mice >6 weeks old were used. To induce pseudoestrus, 100 µl of estradiol valerate was dissolved in sesame oil at 2 mg/ml and injected intraperitoneal at 72 to 96 hours prior to infection and weekly thereafter. 50 ml Cultures of Candida albicans strains were grown overnight at 30° C. Cells were pelleted at 4,000 rpm for 10 minutes, resuspended in 25 ml phosphate buffered saline (PBS) and repeated twice in 10 ml PBS. Cells were then counted with a hemacytometer and diluted in PBS to appropriate density for infection. 20 µl of the inocula (comprising $5 \times 10^4$ cells) was administered from a pipette into the vaginal lumen. The animals were held in an inverted position for 1 min after inoculation (Romani (1999) Current Protocols in Immunology: 19.6.1-19.6.16). The innoculum was left in place for six hours before the first image was acquired.

For example, an infected mouse was imaged on days 1, 2, 3, 5, 6, 7, 9, 13, 15, and 21 post-infection with a light-producing strain of Candida (imaging was carried out by immobilizing the mouse and following the procedures described herein above including administration of the substrate). The time series of in vivo, whole mouse images showed the progressive course of infection clearly imaged by monitoring of the light producing Candida. At day 21 the animals were euthanized the vaginal tissue was excised and examined. This tissue was imaged and presence of the infective agent, that is the light-producing Candida, was clearly demonstrated.

Immediately before imaging, mice were anesthetized with isoflurane for five minutes. In addition to the whole body imaging described above, when asleep, each mouse was held in an inverted position and lavaged with 100 µl of PBS containing 16.6 mg/ml luciferin and 16.6 mM ATP. The pipette tip was inserted into the vaginal lumen and the lavage solution expelled. The lavage solution was aspirated up and down to rinse the lumen walls. Following lavage, most of the luciferin solution was removed and saved in a microcentrifuge tube, leaving about 10-20 µl remaining in the lumen. Lavages from each group of 3 mice were pooled and imaged. Serial dilutions (10×, 100× and 1000×) in PBS were plated on YPD containing 50 mg/ml uridine and 15 µg/ml chloramphenicol. Plates were grown at 30° C. for 24-48 hours and counted. Examination by light microscopy of cell morphology of cells obtained from lavages revealed the presence of virulant, hyphal-forms of Candida cells.

Thus, these results demonstrated that luciferase-containing constructs can be used as reporter constructs in cells that are not amenable to selectable markers. In addition, these results demonstrated that luciferase-containing constructs can be used for high-density screening to detect transformation events and, additionally, allowed for observation in whole animals. By using a luciferase gene from the firefly Photinus pyralis altered to allow its expression in C. albicans, transformed Candida albicans cells were isolated by screening for light production without use of a genetic selection (i.e., employing selectable markers). Typically methods for detection of transformed cells employ selection, either by a nutritional deficiency that is replaced by the introduced DNA, or by drug resistance. For replacement of auxotrophic mutants, the recipient cells have to be deficient in that gene. For drug resistance, the cells have to be sensitive to that drug. Candida albicans, however, is resistant to hygromycin, benomyl, cycloheximide, mitomycin C and tunicamycin (Beckerman, Chibana, et al., (2001) Infect Immun 69(1):108-114). The high-density screening described herein involved no genetic selection and provided an efficient method for obtaining transformants. Successful transformation occurred at a frequency of about $5 \times 10^{-5}$ to $10^{-6}$ (5-10 bioluminescent colonies/5 micrograms of cut DNA) and there was no problem in detecting a transformant (i.e., light producing cells) among the great excess of non transformed cells. The successful transformation demonstrated herein has been repeated with several other virulent strains from ATCC.

All current animal models of *C. albicans* infection involve death as an endpoint or sacrificing the animal, harvesting tissue, plating the homogenate for cell counts and/or sectioning the tissue for histology. Such approaches generally look at a single, late time point in the disease process and do not allow following the course of infection in a single animal. The present invention describes methods to provide bioluminescent cells which can then be imaged in a living infected animal. This allows examination of many temporal and spatial aspects of infection, that are be possible with other methods.

Although preferred embodiments of the subject invention have been described in some detail, it is understood that obvious variations can be made without departing from the spirit and the scope of the invention as defined by the appended claims.

What is claimed is:

1. A method of monitoring a yeast cell infection in a living animal, the method comprising providing a population of the yeast cells; transforming the population of yeast cells with a polynucleotide comprising a luciferase coding sequence operably linked to a promoter; administering the transformed cells to the living animal; and measuring light produced from the luciferase expressed within the transformed cells, in the presence of a luciferase substrate, thereby monitoring the yeast cell infection in the living animal.

2. The method of claim 1, wherein the yeast is *Candida albicans*.

3. The method of claim 1, wherein the polynucleotide comprises an integrating vector.

4. The method of claim 1, wherein the polynucleotide comprises a transposable element or a mobile genetic element, wherein the transposable element or the mobile genetic element comprises the luciferase coding sequence.

* * * * *

SEQUENCE LISTING

```
<160> NUMBER OF SEQ ID NOS: 35

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: primer
      KanF2

<400> SEQUENCE: 1
ctgtagactc gaggagggaa ataataaatg gc                                   32

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: primer
      KanR2

<400> SEQUENCE: 2
cagagtgtcg acagttgcgg atgtac                                          26

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: primer MGC-
      CAT-F1

<400> SEQUENCE: 3
ggtgtccctg ttgataccg                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer
      LuxA-Rev

<400> SEQUENCE: 4
ccacactcct cagagatgcg                                                 20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: XR1T

<400> SEQUENCE: 5
ccgctggaga gcaattgcat aaggct                                          26
```

```
<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: XR1B

<400> SEQUENCE: 6
agccttatgc aattgctctc cagcgg                                              26

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: XR2T

<400> SEQUENCE: 7
gaagagatac gccttggttc ctgc                                                24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: XR2B

<400> SEQUENCE: 8
ccaggaacca aggcgtatct cttc                                                24

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: XR3T

<400> SEQUENCE: 9
aaacgatatg gttgaataca aatcac                                              26

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: XR3B

<400> SEQUENCE: 10
gtgatttgta ttcaacccat atcgttt                                             27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: XR4T

<400> SEQUENCE: 11
gtgacaaaac aattgcattg ataatga                                             27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: XR4B

<400> SEQUENCE: 12
```

```
tcattatcaa tgcaattgtt ttgtcac                                         27

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: RR1T

<400> SEQUENCE: 13
gatttgaaga agagttgttt ttacgatccc tt                                   32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: RR1B

<400> SEQUENCE: 14
aagggatcgt aaaaacaact cttcttcaaa tc                                   32

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: RR2T

<400> SEQUENCE: 15
cgccaaaagc acattgattg acaaata                                         27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: RR2B

<400> SEQUENCE: 16
tatttgtcaa tcaatgtgct tttggcg                                         27

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: RR3T

<400> SEQUENCE: 17
agactacatc tgctattttg attacaccc                                       29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: RR3B

<400> SEQUENCE: 18
gggtgtattc aaaatagcag atgtagtct                                       29

<210> SEQ ID NO 19
<211> LENGTH: 45
<212> TYPE: DNA
<213> ORGANISM: Artificial Sequence
```

```
<220> FEATURE:
<223> OTHER INFORMATION: Description of Artificial Sequence: RR45T

<400> SEQUENCE: 19
aggttgtgga tttggataca gggaaaactt tgggcgttaa tcaga                    45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: RR45B

<400> SEQUENCE: 20
tctgattaac gcccaaagtt ttccctgtat ccaaatccac aacct                    45

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Asc I
      linker

<400> SEQUENCE: 21
aggcgcgcct                                                           10

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: ENOA

<400> SEQUENCE: 22
tagggcgcgc cagatttgtt tacaggtgat gctt                                34

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: ENOB

<400> SEQUENCE: 23
tatggatcct gttgtaatat tcctgaatta tca                                 33

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: LUCB

<400> SEQUENCE: 24
tggggatcca tggaagacgc caaaaacata agaaagg                             38

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: LUCP

<400> SEQUENCE: 25
tatgctgcag ttacaatttg gactttccgc                                     30
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: ACT-TP

<400> SEQUENCE: 26
gttctgcagg agtgaaattc tggaaatct                                        29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: ACT-TH

<400> SEQUENCE: 27
gttaagcttt ttatggaatg aatgggatg                                        29

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: URAH

<400> SEQUENCE: 28
gtaaagctta ctaataggaa ttgatttgga tggt                                  34

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: URAF

<400> SEQUENCE: 29
gtacggccgg ccaggaccac ctttgattgt aaatag                                36

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: TAR5N

<400> SEQUENCE: 30
gtagcggccg cgaggagtaa aacttttcca attaac                                36

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: TAR5A

<400> SEQUENCE: 31
gtaggcgcgc cacttttttct tcattaccat aaaccc                               36

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: TAR3F -continued

```
<400> SEQUENCE: 32
gtatggccgg ccttgagata agtagggttt gatagcc                                37

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: TAR3S

<400> SEQUENCE: 33
atgtcctgca ggctcgggta ccacactgtt agataaa                                37

<210> SEQ ID NO 34
<211> LENGTH: 59
<212> TYPE: DNA
<213> ORGANISM: Artificial Sequence
<220> FEATURE:
<223> OTHER INFORMATION: Description of Artificial Sequence: synthetic
      linker A

<400> SEQUENCE: 34
ggccggcatt ggcgcgccta taagcttcac atctggccgg ccgactcctg caggatctc        59

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: synthetic
      linker B

<400> SEQUENCE: 35
tcgagagatc ctgcaggagt gggccggcca gatgaagctt ataggcgcgc caatgcggcc       60
```